US009802878B2

(12) United States Patent
Nakamura et al.

(10) Patent No.: US 9,802,878 B2
(45) Date of Patent: Oct. 31, 2017

(54) METHOD FOR PRODUCING TRIFLUOROETHYLENE

(71) Applicant: Asahi Glass Company, Limited, Chiyoda-ku (JP)

(72) Inventors: Masahiko Nakamura, Chiyoda-ku (JP); Hidekazu Okamoto, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 15/218,120

(22) Filed: Jul. 25, 2016

(65) Prior Publication Data
US 2016/0332938 A1 Nov. 17, 2016

Related U.S. Application Data

(63) Continuation of application No. PCT/JP2015/052527, filed on Jan. 29, 2015.

(30) Foreign Application Priority Data

Jan. 30, 2014 (JP) .................................. 2014-015962

(51) Int. Cl.
*C07C 17/25* (2006.01)
*C07C 21/18* (2006.01)
(Continued)

(52) U.S. Cl.
CPC ............. *C07C 17/25* (2013.01); *B01J 8/1818* (2013.01); *B01J 8/1827* (2013.01); *B01J 23/02* (2013.01);
(Continued)

(58) Field of Classification Search
CPC ...................................................... C07C 17/25
See application file for complete search history.

(56) References Cited

U.S. PATENT DOCUMENTS 5,856,593 A * 1/1999 Powell .................... C07C 17/25
570/156
8,373,010 B2 * 2/2013 Merkel ................. C07C 17/206
570/155
2011/0207904 A1 8/2011 Murai et al.

FOREIGN PATENT DOCUMENTS

JP 5-17425 1/1993
JP 6-56705 3/1994
(Continued)

OTHER PUBLICATIONS

Gillet, D. et al. WO2011157907 A1, Dec. 2011, pp. 1-5; English translation.*

(Continued)

*Primary Examiner* — Medhanit Bahta
(74) *Attorney, Agent, or Firm* — Oblon, McClelland, Maier & Neustadt, L.L.P.

(57) ABSTRACT

A method to stably produce trifluoroethylene with a high selectivity by reacting 1,1,1,2-tetrafluoroethane with a solid reactant and suppressing the formation of by-products such as polymer carbon is provided. In the method, a material gas containing 1,1,1,2-tetrafluoroethane passes through a layer consisting of a particulate solid reactant having an average particle size of from 1 μm to 5,000 μm to bring the solid reactant and 1,1,1,2-tetrafluoroethane into contact with each other in a state where the layer consisting of the solid reactant is fluidized.

12 Claims, 11 Drawing Sheets

(51) Int. Cl.
 *B01J 23/02* (2006.01)
 *B01J 27/232* (2006.01)
 *B01J 8/18* (2006.01)
 *C09K 5/04* (2006.01)

(52) U.S. Cl.
 CPC ............ *B01J 27/232* (2013.01); *C09K 5/045* (2013.01); *B01J 2208/0007* (2013.01); *B01J 2208/00407* (2013.01); *B01J 2208/00415* (2013.01); *C09K 2205/126* (2013.01)

(56) References Cited

FOREIGN PATENT DOCUMENTS

| | | |
|---|---|---|
| JP | 10-505337 | 5/1998 |
| JP | 2007-500127 A | 1/2007 |
| JP | 2010-70489 | 4/2010 |
| JP | 2010-533151 | 10/2010 |
| JP | 5722623 | 5/2015 |
| WO | WO 2011/157907 A1 | 12/2011 |
| WO | WO 2014/178353 A1 | 11/2014 |

OTHER PUBLICATIONS

International Search Report issued Apr. 21, 2015 in PCT/JP2015/052527, filed on Jan. 29, 2015.
Takashi Shirai "Ryudo Shokubai, Ryudoso no Shikenho", Chemical Engineering of Japan, 1963, 4 pages.
Joachim Werther, "Fluidized-Bed Reactors", Ullmann's Encyclopedia of Industrial Chemistry, Hamburg University of Technology, Hamburg, Germany, Oct. 15, 2007, pp. 1-50.

* cited by examiner

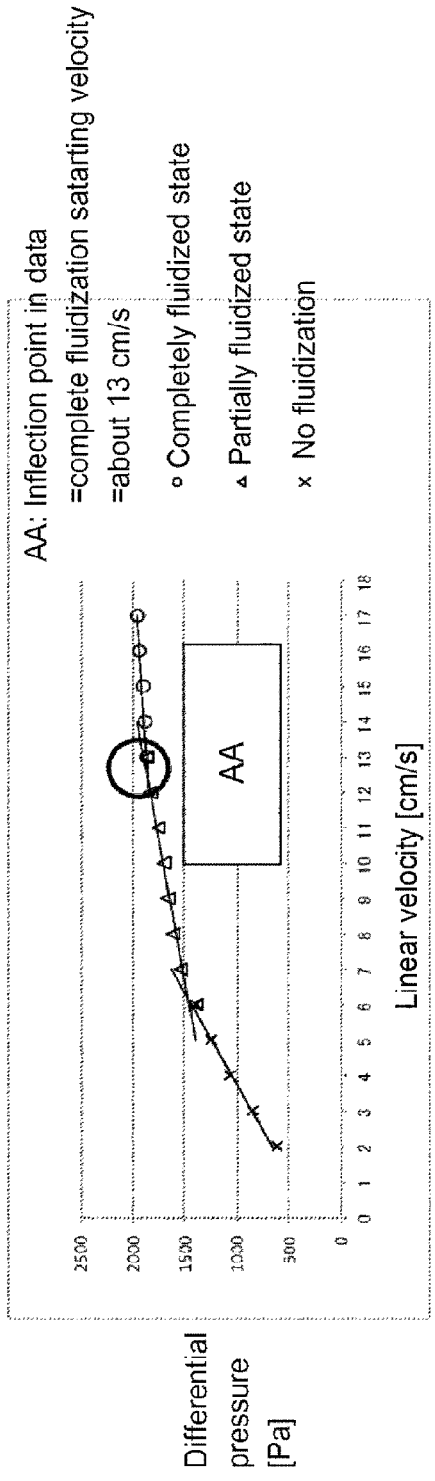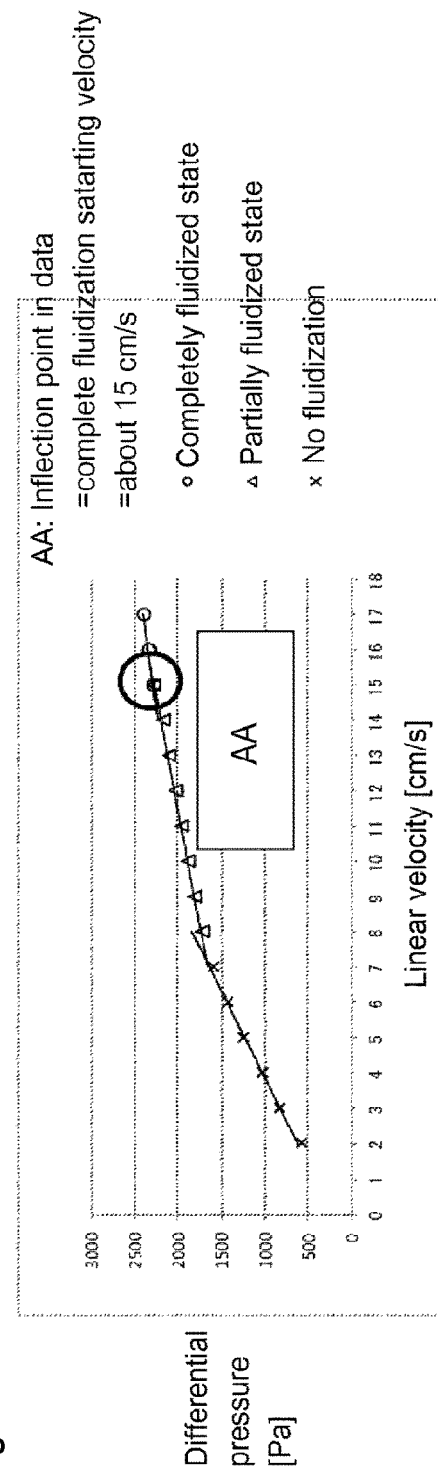

METHOD FOR PRODUCING TRIFLUOROETHYLENE

TECHNICAL FIELD

The present invention relates to a method for producing trifluoroethylene, more particularly, a method for efficiently producing trifluoroethylene from 1,1,1,2-tetrafluoroethane.

BACKGROUND ART

Trifluoroethylene (HFO-1123), which has a low global warming potential (GWP), is greatly expected in recent years as a new refrigerant which may replace difluoromethane (HFC-32) and 1,1,1,2,2-pentafluoroethane (HFC-125) which are greenhouse gases.

In this specification, abbreviated names (e.g. refrigerant numbers) of halogenated hydrocarbon compounds are described in brackets after the compound names. As the case requires, the abbreviated names are employed instead of the compound names.

Heretofore, a method for producing HFO-1123 from 1,1,1,2-tetrafluoroethane (HFC-134a) which is a relatively inexpensive material has been known. For example, Patent Document 1 discloses a method of subjecting HFC-134a to dehydrofluorination in a gaseous phase using a metal fluoride as a catalyst. Further, Patent Document 2 discloses a method of reacting HFC-134a with a metal hydroxide such as calcium hydroxide in a gaseous phase.

However, either of the methods disclosed in Patent Documents 1 and 2 has the following problems since HFC-134a in a gaseous phase is brought into contact with and reacted with a solid reactant forming a fixed bed.
(1) Since it is difficult to uniformly mix particles of the solid reactant with HFC-134a and bring them into contact with each other, the degree of conversion of the solid reactant is low. Further, since the reactivity in the reaction of forming HFO-1123 from HFC-134a is low, it is necessary to bring HFC-134a into contact with the solid reactant for a long period of time.
(2) Since the heat removal efficiency is poor when a fixed bed is used, hot spots are likely to form. Accordingly, side reactions such as cleavage of a carbon-carbon bond of HFC-134a are likely to occur, and by-products such as low molecular weight hydrocarbon compounds such as methane, ethylene and propylene and polymer carbon (graphite) are likely to form.
(3) Since the amount of by-products such as polymer carbon is large, the polymer carbon is attached to the surface of the solid reactant, whereby the degree of conversion of HFC-134a is remarkably lowered with time. Thus, stable production of HFO-1123 is difficult.

PRIOR ART DOCUMENTS

Patent Documents

Patent Document 1: JP-A-2010-533151
Patent Document 2: WO2011/157907

DISCLOSURE OF INVENTION

Technical Problem

The present invention has been made to solve the above problems, and its object is to provide a method for producing HFO-1123 stably with a high selectivity, by efficiently reacting HFC-134a which is an inexpensive material with a solid reactant, while formation of by-products such as low molecular weight hydrocarbon compounds and polymer carbon is suppressed.

Solution to Problem

The method for producing HFO-1123 of the present invention comprises making a material gas containing HFC-134a to flow through a layer consisting of a particulate solid reactant having an average particle size of from 1 μm to 5,000 μm to bring the solid reactant and HFC-134a into contact with each other in a state where the layer consisting of the solid reactant is fluidized.

In the present invention, "in a state where the layer consisting of a solid reactant (hereinafter sometimes referred to as a solid reactant layer) is fluidized" is a state created by extruding a fluid such as a material gas upward (in a direction opposite to the direction of gravitational force) and is a state in which particles of the solid reactant are suspended and floating in the fluid. The upward drag by a fluid flow, the gravity and the buoyancy acting on the solid particles are balanced, and the entire solid reactant layer behaves as a uniform fluid. On that occasion, the pressure loss when the fluid passes through the solid reactant layer is equal to a difference between the gravity and the buoyancy, and so long as a fluidized state is maintained, the pressure loss of the solid reactant layer is always constant at a difference between the gravity and the buoyancy even when the flow velocity of the fluid is changed. A solid reactant layer in such a fluidized state will be referred to as a fluid bed or a fluidized bed.

In a case where the solid reactant layer is "in a fluidized state", particles of the solid reactant constituting the layer float and flow in the fluid, and thus the term "fluidized state" refers to both the solid reactant layer and the particles of the solid reactant.

Advantageous Effects of Invention

According to the present invention, in production of HFO-1123 from HFC-134a, sufficiently high degree of conversion of 134a and selectivity for HFO-1123 are achieved and in addition, formation of hot spots in the reaction site can be prevented, and formation of by-products such as low molecular weight hydrocarbon compounds and polymer carbon can be suppressed, whereby HFO-1123 can be obtained efficiently and stably.

Further, the production method of the present invention has an advantage over a method of bringing HFC-134a in a gaseous phase into contact with a solid reactant in a fixed bed and reacting them, as follows.

That is, by the reaction in the fluidized bed, the efficiency of removal of the heat of reaction is high and hot spots are less likely to form, and thus progress of side reaction (cleavage of carbon-carbon bond) of HFC-134a can be suppressed. Accordingly, low molecular weight hydrocarbon compounds and polymer carbon (graphite) are less likely to form as by-products, and the selectivity for the reaction for formation of R-1123 tends to improve. Further, since polymer carbon is less likely to form as a by-product, a decrease in the degree of conversion of HFC-134a with time caused by attachment of the polymer carbon to the surface of the solid reactor tends to be prevented, and R-1123 will be stably obtained.

And, HFO-1123 obtained by the production method of the present invention is useful as a refrigerant which replaces HFC-32 and HFC-125 which are greenhouse gases, and as a material monomer and a synthetic intermediate of a functional material such as a piezoelectric element or a film.

As described above, according to the production method of the present invention, it is possible to produce HFO-1123 useful as a new refrigerant and as a material monomer or a synthetic intermediate of a functional material, from HFC-134a as a material, by an efficient method with a high degree of conversion of HFC-134a and a high selectivity for HFO-1123, and with small loss due to formation of impurities. Further, since side reactions such as cleavage of a carbon-carbon bond of HFC-134a can be suppressed and polymer carbon is less likely to form as a by-product, a decrease in the degree of conversion of HFC-134a with time can be prevented, and HFO-1123 can be produced stably over a long period of time.

BRIEF DESCRIPTION OF DRAWINGS

FIG. 4 is a graph obtained by plotting a differential pressure relative to a linear velocity of a nitrogen gas in Fluidization Example 1.

FIG. 5 is a graph obtained by plotting a differential pressure relative to a linear velocity of a gas mixture of HFC-134a and nitrogen in Fluidization Example 2.

DESCRIPTION OF EMBODIMENTS

Figure 1:
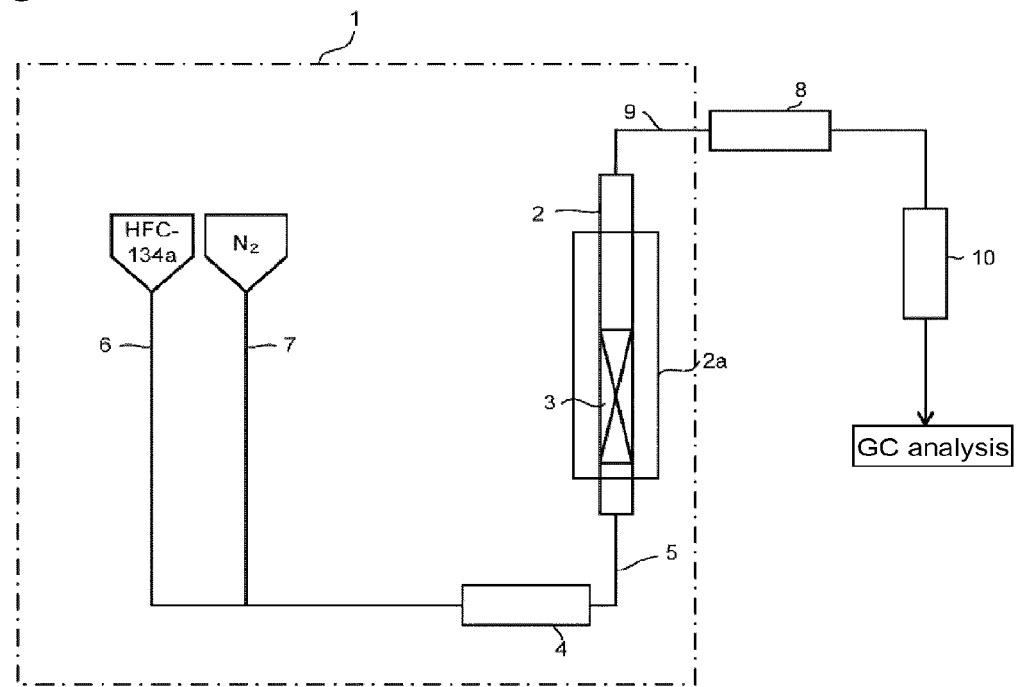
FIG. 1 is a drawing illustrating an example of a fluidized bed reaction apparatus used in the production method of the present invention.

Now, an embodiment of the present invention will be described. The present invention is by no means restricted to the following embodiment.

The production method according to an embodiment of the present invention comprises making a material gas containing HFC-134a to flow through a layer consisting of a particulate solid reactant having an average particle size of from 1 μm to 5,000 μm, to fluidize the layer consisting of the solid reactant, thereby to bring particles of the solid reactant in a fluidized state and HFC-134a into contact with each other, whereby dehydrofluorination of HFC-134a is made to progress and HFO-1123 is produced. Such a reaction of the solid reactant in a fluidized state and HFC-134a by contact is carried out by using a fluidized bed reaction apparatus which has a fluid bed (fluidized bed) consisting of the solid reactant formed in a reactor.

The reaction of HFC-134a with the solid reactant in the production method of the present invention may be represented by the following reaction formula (1) or (2) as a representative example. The reaction formula (1) represents a reaction in a case where the solid reactant functions as a catalyst (Cat.), and the reaction formula (2) represents a reaction in a case where the solid reactant functions as a basic reactant (MOH: M represents a metal).

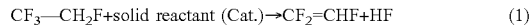

$$CF_3-CH_2F + \text{solid reactant (Cat.)} \rightarrow CF_2=CHF + HF \quad (1)$$

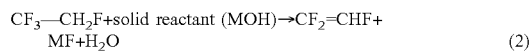

$$CF_3-CH_2F + \text{solid reactant (MOH)} \rightarrow CF_2=CHF + MF + H_2O \quad (2)$$

When HFC-134a is brought into contact with the solid reactant, dehydrofluorination reaction occurs in which one of fluorine atoms bonded to a carbon atom to which three fluorine atoms are bonded between the two carbon atoms of HFC-134a, and one of hydrogen atoms bonded to the other carbon atom, leave simultaneously. And, by such dehydrofluorination reaction of HFC-134a, HFO-1123 forms. On that occasion, the fluorine atom and the hydrogen atom which have left form hydrogen fluoride when the solid reactant functions as a catalyst, and form a metal fluoride (MF) and water simultaneously when the solid reactant functions as a basic reactant.

According to the production method of the present invention, by contact of HFC-134a with the solid reactant, HFC-134a is brought into contact with the particulate solid reactant having an average particle size of from 1 μm to 5,000 μm which forms a fluidized bed and is in a fluidized state, whereby HFC-134a is reacted with a sufficiently high degree of conversion, and HFO-1123 can be obtained with a high selectivity.

(Fluidized Bed Reaction Apparatus)

As a reaction apparatus in the embodiment of the present invention, a fluidized bed reaction apparatus is employed. As the fluidized bed type reaction apparatus, a fluid bed type reaction apparatus or a riser type reaction apparatus may be employed. With a view to stably producing HFO-1123 efficiently, a fluid bed type reaction apparatus is preferred.

A fluid bed type reaction apparatus comprises, for example, a reactor (hereinafter sometimes referred to as a fluidized bed reactor) in which a fluid bed (fluidized bed) is formed and as the case requires, in the interior of the reactor, a cooling coil for heat removal or an electric heater to heat the interior. Further, it has a cyclone which separates the material gas or the reaction gas from the solid reactant on the upper portion in the interior of the reactor. The cyclone may be disposed on the outside of the reactor. Further, it has a gas dispersing apparatus to supply a material gas at the bottom and/or at the lower portion of the reactor. As the material of the reactor, glass, iron, nickel, or an alloy containing iron or nickel as the main component may, for example, be used.

In the production method of the present invention, each of supply of the material gas containing HFC-134a and supply of the solid reactant to the fluidized bed reactor may be carried out continuously, or only supply of the material gas containing HFC-134a may be carried out continuously, and the solid reactant is supplied by the batch. Now, the method of the present invention will be described with reference to a case where only the material gas containing HFC-134a is continuously supplied, and the solid reactant is supplied to the fluidized bed reactor by the batch, however, the present invention is by no means restricted thereto.

(Material Gas Containing HFC-134a)

The material gas containing HFC-134a used in the present invention is present always in a gaseous phase under the after-mentioned reaction conditions. HFC-134a may be HFC-134a with a purity of 100% (mol %), or may be one containing 1,1,2,2-tetrafluoroethane (HFC-134) which is an impurity derived from the production method.

In a case where it contains HFC-134a, the purity of HFC-134a is preferably at least 50 mol %. That is, the material gas may be one containing HFC-134a with a purity of 100% (mol %) or may be one containing HFC-134a with a purity of 50 mol % containing impurities such as HFC-134.

From the viewpoint of suppression of side reaction and stable progress of fluidized bed reaction, the material gas preferably contains, in addition to HFC-134a with a purity of at least 50 mol %, an inert gas such as nitrogen, argon or helium. By such a gas, HFC-134a as a reaction component can be diluted. Hereinafter such a gas will be referred to as a diluent gas. Further, incorporation of such a diluent gas is preferred also from the viewpoint of easiness of supply of HFC-134a to the reactor and adjustment of the flow rate.

In a case where the material gas contains a diluent gas, the content of the diluent gas is preferably at most 95 mol %, particularly preferably at most 50 mol % based on the entire amount of the material gas containing HFC-134a, in view of the reaction efficiency, suppression of side reaction, etc. Further, the content of HFC-134a based on the entire amount of the material gas is preferably at least 5 mol % and less than 100 mol %, particularly preferably at least 50 mol % and less than 100 mol %.

In an embodiment in which the material gas containing HFC-134a and the solid reactant are continuously brought into contact with each other and reacted, by controlling the flow rates of the respective components (HFC-134a and the diluent gas) constituting the material gas per unit time, the molar ratio of the respective components in the material gas can be controlled.

(Solid Reactant)

The solid reactant used in the present invention is a particulate solid reactant having an average particle size of from 1 µm to 5,000 µm. In this specification, the average particle size is a value measured by a laser diffraction/scattering particle size analyzer.

If the average particle size of the solid reactant is less than 1 µm, adhesion property of particles tends to be high, and when the material gas containing HFC-134a is made to flow through and is brought into contact with the solid reactant layer, the solid reactant layer is less likely to be fluidized, whereby uniform mixing and contact of the particles of the solid reactant with HFC-134a tend to be difficult, and the degree of conversion of HFC-134a tends to be low. Further, the heat removal efficiency in the solid reactant layer as the reaction site tends to be low, and hot spots are likely to form, whereby side reactions such as carbonization are likely to occur, and due to adhesion of a carbon compound, the degree of conversion of HFC-134a will be decreased with time. On the other hand, if the average particle size of the solid reactant exceeds 5,000 µm, the velocity of flow of the material gas necessary to fluidize the particles of the solid reactant tends to be too high. Accordingly, in order to secure a sufficient contact time for the reaction with HFC-134a, a large-sized reactor is necessary, and the production efficiency tends to be low.

As mentioned above, if the average particle size of the solid reactant is out of the range of from 1 µm to 5,000 µm, even if HFC-134a is made to flow through the solid reactant layer, it tends to be difficult to fluidize the solid reactant layer sufficiently to secure uniform contact with HFC-134a. Thus, it tends to be difficult to achieve a sufficiently high degree of conversion of HFC-134a thereby to stably produce HFO-1123 with a high selectivity. The average particle size of the solid reactant is preferably within a range of from 40 µm to 5,000 µm, more preferably from 40 µm to 500 µm.

Here, the fluidized state of the solid reactant layer may be examined, for example, by (a) visual observation or by (b) measuring a differential pressure.

(a) Visual Observation

Whether the upper portion and the lower portion of the solid reactant layer are mixed is visually observed, and the fluidized state is evaluated on the basis of the following standards.

Completely fluidized state: The upper portion and the lower portion are mixed in the entire solid reactant layer.

Partially fluidized state: The upper portion and the lower portion are mixed in a part of the solid reactant layer.

Non-fluidized state: The upper portion and the lower portion of the solid reactant layer are not mixed.

(b) Measuring Differential Pressure

A difference in the gas pressure between on the inlet side and on the outlet side of a reactor (hereinafter referred to as a differential pressure) is measured. And, a graph is prepared by plotting the differential pressure relative to the velocity of flow (for example, the after-mentioned linear velocity) of a gas, and the start of fluidization is determined by the presence of an inflection point.

Such determination of the fluidized state of the solid reactant layer will be described in further detail in Examples.

When the solid reactant is brought into contact with the material gas containing HFC-134a, the solid reactant may be in a solid phase or may be dispersed in a medium in a liquid phase. As a solvent in which the solid reactant is dispersed, for example, water, an alcohol solvent such as methanol or ethanol, or a chlorinated solvent such as carbon tetrachloride may be mentioned. Since by contact in a state where the solid reactant is dispersed in a medium in a liquid phase, the pressure in the reaction system tends to be too high and high temperature reaction tends to be difficult, and accordingly it is preferred that the solid reactant is a solid phase and is brought into contact with the material gas in a gaseous phase.

The specific surface area of the solid reactant is preferably from 1 to 400 m$^2$/g, more preferably from 1 to 200 m$^2$/g. In this specification, the specific surface area is a value measured by a BET method (BET specific surface area). If the specific surface area of the solid reactant is less than 1 m$^2$/g, the reaction rate tends to be low, and the reaction efficiency tends to be low. Further, if the specific surface are exceeds 400 m$^2$/g, the density of the solid reactant particles tends to be too low, and thus the particles are likely to fly and the handling efficiency is thereby low.

The bulk density of the solid reactant is preferably from 0.2 to 3.0 g/cm$^3$, more preferably from 0.5 to 2.9 g/cm$^3$, particularly preferably from 0.7 to 2.5 g/cm$^3$. If the bulk density of the solid reactant is less than 0.2 g/cm$^3$, the volume at the same mass tends to be large, and not only a large-sized reactor is necessary, but also the particles of the solid reactant are likely to fly and the handling efficiency is thereby low, thus leading to a poor production efficiency. Further, if the bulk density of the solid reactant is higher than 3.0 g/cm$^3$, the rate of the material gas required to fluidize the particles of the solid reactant tends to be too high. Accordingly, in order to secure a sufficient contact time for the reaction with HFC-134a, a large-sized reactor will be necessary, and the production efficiency tends to be poor.

The solid reactant used in the present invention contains a compound which relates to the reaction mechanism represented by the reaction formula (1) or (2) as a representative example. The compound which may relate to the reaction mechanism represented by the reaction formula (1) or (2) as a representative example may, for example, be at least one compound selected from a metal oxide, a metal hydroxide, a metal carbonate, a metal sulfate and a metal halide. Preferred is a metal oxide or a metal carbonate, whereby HFC-134a will be efficiently converted to HFO-1123. The solid reactant may be used alone or in combination of two or more.

The metal species contained in the metal compound may be an alkali metal, an alkaline earth metal, a transition metal, a group 12 metal, a group 13 metal or a group 14 metal. Among them, preferred is an alkali metal, an alkaline earth metal, a group 13 metal or a group 14 metal, particularly preferred is sodium, potassium, calcium, magnesium, aluminum or silicon.

The metal oxide may be an oxide of one of the above metals or may be a composite oxide of two or more metals.

The metal hydroxide may be a hydroxide of one of the above metals or may be a composite hydroxide of two or more metals.

The metal carbonate may be a carbonate of one of the above metals or may be a composite carbonate of two or more metals.

The metal sulfate may be a sulfate of one of the above metals or may be a composite sulfate of two or more metals.

The metal halide may be a halide of one of the above metals or may be a composite halide of two or more metals.

Specifically, the solid reactant may, for example, be potassium carbonate, calcium hydroxide, calcium oxide, magnesium oxide, aluminum fluoride or aluminum oxide (alumina). In order that HFC-134a is converted to HFO-1123 efficiently, the solid reactant is particularly preferably potassium carbonate or calcium oxide.

The solid reactant in the present invention may be constituted solely by the above compound which may relate to the reaction mechanism represented by the reaction formula (1) or (2) as a representative example or may contain another component. Such another component which the solid reactant may contain may, for example, be a carrier to support the compound which may relate to the reaction mechanism represented by the reaction formula (1) or (2) as a representative example. The carrier may, for example, be an alumina carrier, a zirconia carrier, a silica carrier, a silica-alumina carrier, a carbon carrier represented by activated carbon, a barium sulfate carrier or a calcium carbonate carrier. Activated carbon may, for example, be activated carbon prepared from a material such as wood, charcoal, fruit shell, coconut shell, peat, lignite or coal.

(Reaction Conditions)

The material gas containing HFC-134a may be introduced to a reactor (for example, a fluidized bed reactor) as it is at room temperature, but is preferably heated (preheated) before introduced to a reactor and then supplied, so as to increase the reactivity. In a case where it is preheated, the material gas is preferably heated to a temperature of from 80 to 450° C. and then supplied to a reactor. Further, the respective components (HFC-134a and the diluent gas) in the material gas containing HFC-134a may be respectively preheated to the above temperature and then mixed, and the mixed material gas at the above temperature is supplied to a reactor, or the respective components may be mixed first, and then the material gas is heated to the above temperature and supplied to a reactor. Further, the respective components for the material gas may be respectively preheated to the above temperature and separately supplied to a reactor.

When the material gas containing HFC-134a is supplied, in order that the linear velocity of the material gas in the reactor is within a predetermined range, the flow rates per unit time (hereinafter referred to simply as flow rate) of HFC-134a and the diluent gas are preferably set. The linear velocity of the material gas is preferably from 1 cm/s to 1,000 cm/s, more preferably from 1 cm/s to 20 cm/s. Here, the linear velocity means a superficial velocity, and is calculated, assuming that the reactor through which the material gas flows is a void tower having no content in the interior thereof, by dividing the flow rate (volume flow rate) at the temperature under the pressure in the interior of the reactor by the cross section area of the reactor which is a void tower.

Linear velocity (superficial velocity) (cm/s)= flow rate (cm$^3$/s)/cross section area (cm$^2$)

In such a manner, the material gas containing HFC-134a introduced to the reactor is brought into contact with the solid reactor in a fluidized state forming the fluid bed (fluidized bed) in the reactor for a predetermined time. The temperature at the time of contact is preferably from 50 to 500° C., more preferably from 100 to 500° C., particularly preferably from 350 to 500° C. as the temperature in the interior of the reactor, with a view to improving the reactivity. The pressure in the reactor is preferably from 0 to 5 MPa, more preferably from 0 to 1 MPa by the gauge pressure. The contact time of HFC-134a and the solid reactant in the reactor is preferably from 0.1 to 500 seconds, more preferably from 0.1 to 100 seconds, further preferably from 0.1 to 20 seconds.

(Reaction Apparatus)

An example of a reaction apparatus used for production of HFO-1123 in the present invention is shown in FIG. 1. A fluidized bed reaction apparatus 1 shown in FIG. 1 comprises an electric furnace or an electric heater 2a and in its inside, a vertical fluidized bed reactor 2. A heating means such as an electric furnace or an electric heater 2a is not essential.

In the fluidized bed reactor 2, a solid reactant layer 3 of e.g. potassium carbonate is accommodated to form a vertical fluidized bed. Further, to the lower portion of the fluidized bed reactor 2, a preheating mixer 4 provided with a heating means such as an electric heater is connected via a material gas supply line 5. The material gas supply line 5 is preferably also provided with a heating means such as an electric heater. To the preheating mixer 4, a HFC-134a supply line 6 to supply HFC-134a which is gaseous at room temperature and a diluent gas supply line 7 which supplies a diluent gas are connected. HFC-134a and a diluent gas are supplied to the preheating mixer 4 respectively from the HFC-134a supply line 6 and the diluent gas supply line 7, mixed in the preheating mixer 4 and heated to a predetermined temperature, and the mixture is supplied to the fluidized bed reactor 2 through the material gas supply line 5.

Further, as shown in FIG. 1, the HFC-134a supply line 6 and the diluent gas supply line 7 may be combined before the preheating mixer 4, so that HFC-134a and the diluent gas are mixed and the mixture is supplied to the preheating mixer 4 via a gas mixture supply line (not shown), or the HFC-134a supply line 6 and the diluent gas supply line 7 may be respectively connected to the preheating mixer 4, so that HFC-134a and the diluent gas are separately supplied to the preheating mixer 4. Further, at least one of the HFC-134a supply line 6 and the diluent gas supply line 7 may be provided with a preheater (not shown) provided with e.g. an electric heater, so that at least one of HFC-134a and the diluent gas supplied through the line is heated and then introduced to the preheating mixer 4.

To the outlet on the upper portion of the fluidized bed reactor 2, an outlet line 9 provided with a heating means 8 such as an electric heater is connected, and the outlet line 9 is provided with a hydrogen fluoride trapping tube 10. Hydrogen fluoride is removed from a gas discharged from the outlet of the fluidized bed reactor 2 (hereinafter referred to as an outlet gas) by the hydrogen fluoride trapping tube 10, and the outlet gas is collected into a sampling bag, and its components are analyzed by an analyzer such as a gas chromatograph (GC) and determined.

(Outlet Gas Component)

In the production method of the present invention, HFO-1123 can be obtained as a component in the outlet gas. Compounds other than HFO-1123 and an unreacted material component (HFC-134a) contained in the outlet gas may, for example, be hydrogen fluoride, E/Z-1,2-difluoroethylene (E/Z-HFO-1132), 1,1-difluoroethylene (VdF), 1,1,2-trifluoroethane (HFC-143), methane, ethane, ethylene, propane, propylene, n-butane, isobutane, 1-n-butene, 2-n-butene, isobutene, fluoroethylene (HFO-1141), 3,3-difluoropropene (HFO-1252zf), 3,3,3-trifluoropropene (HFO-1243zf), 2,3,3,3-tetrafluoropropene (HFO-1234yf), E/Z-1,3,3,3-tetrafluoropropene (E/Z-HFO-1234ze), hexafluoropropylene (HFP), HFC-125, HFC-134, 1,1,1-trifluoroethane (HFC-143a), 1,1,1,2,2,3,3-heptafluoropropane (HFC-227ca), 1,1,1,2,3,3,3-heptafluoropropane (HFC-227ea), 1,1,1,3,3,3-hexafluoropropane (HFC-236fa), 1,1,1,2,3,3-hexafluoropropane (HFC-236ea), HFC-32, trifluoromethane (HFC-23), fluoromethane (HFC-41), carbon monoxide, carbon dioxide and water. In the above description, E/Z means a mixture of E-form and Z-form.

The compound obtained as the outlet gas component may be used as it is for various applications, but is preferably used after purification to improve the purity of HFO-1123 as a desired component. The purification method may, for example, be distillation, adsorption or washing with an acidic aqueous solution, a basic aqueous solution or a neutral aqueous solution. The components other than HFO-1123 contained in the outlet gas may be separated and removed to a desired extent by the above means. Among the above purification methods, preferred is distillation under normal pressure, elevated pressure or reduced pressure, and by distillation under such a pressure, high purity HFO-1123 can be obtained. Further, HFC-134a separated from the outlet gas may be recycled as a part of the material gas.

EXAMPLES

Now, the present invention will be described in detail with reference to Examples. However, it should be understood that the present invention is by no means restricted to such specific Examples. In the following description, the preheat temperature of HFC-134a, and the temperature and the pressure in the reactor are set values.

A. Synthesis Reaction Using Potassium Carbonate as Solid Reactant (Analysis Conditions)

To analyze the composition of the outlet gas, gas chromatography (GC) was employed. As a column, DB-1 (manufactured by Agilent Technologies, length: 60 m×inner diameter: 250 μm×thickness: 1 μm) was used.

(Reaction Apparatus 1)

Figure 2:
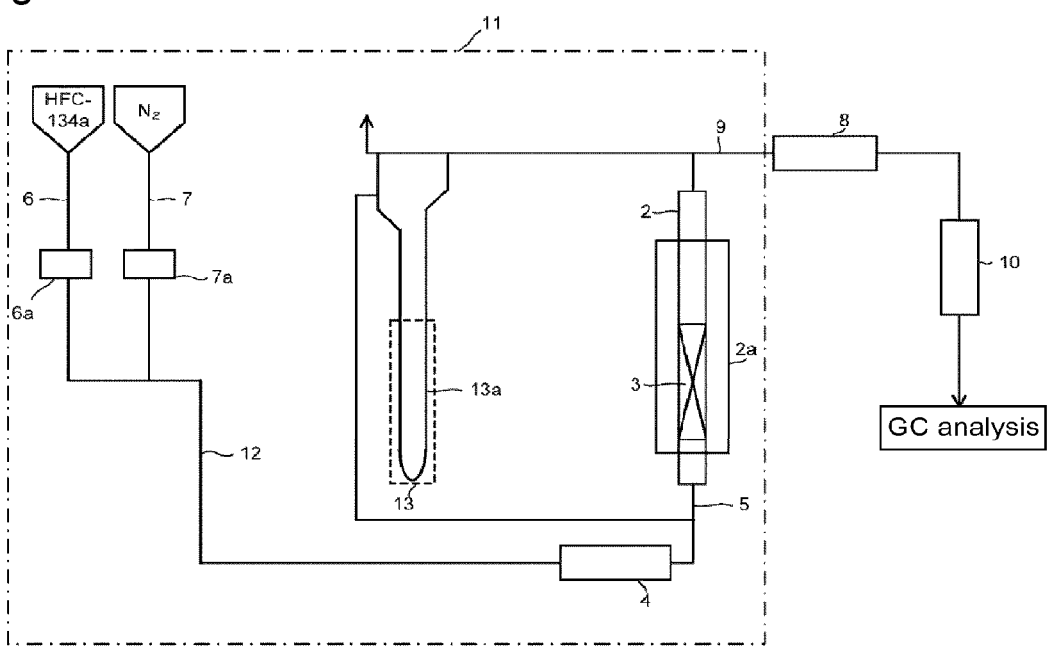
FIG. 2 is a diagram illustrating a fluidized bed reaction apparatus provided with a differential pressure measuring device used in Examples of the present invention.
Figure 3:
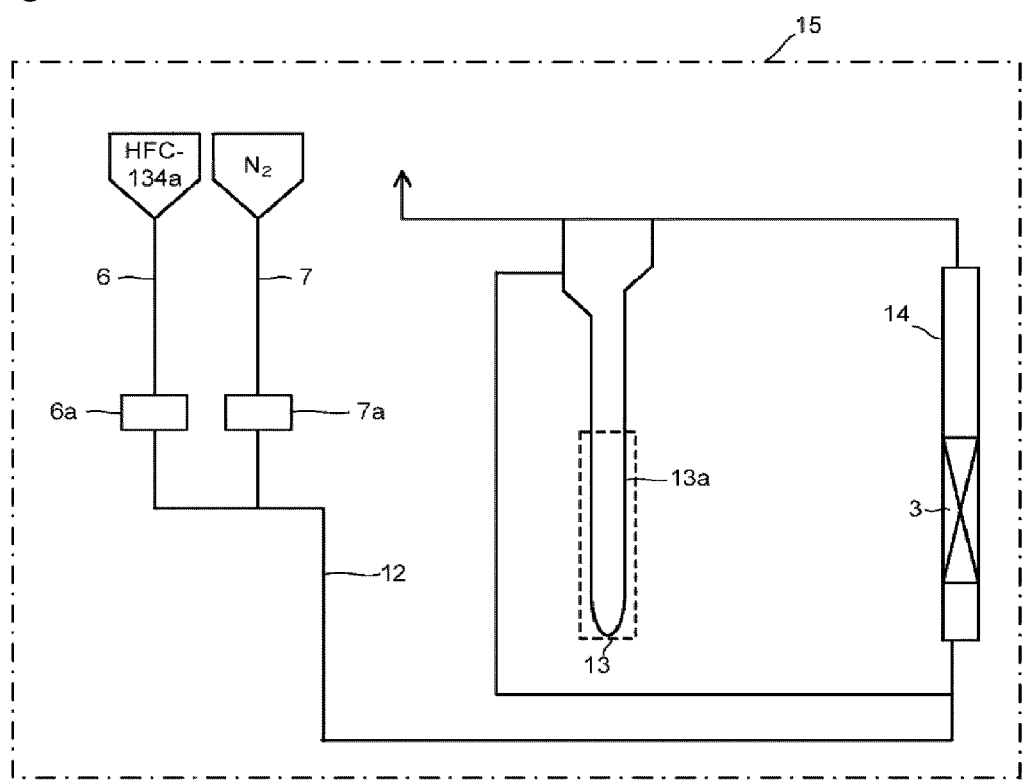
FIG. 3 is a drawing illustrating a fluidization visualized test apparatus provided with a differential pressure measuring device used in Examples of the present invention.

As a reaction apparatus 1, a fluidized bed reaction apparatus 11 shown in FIG. 2 was used. The fluidized bed reaction apparatus 11 shown in FIG. 2 comprises the fluidized bed reaction apparatus 1 shown in FIG. 1, provided with a differential pressure measuring device to measure a differential pressure between on the inlet side and on the outlet side of the fluidized bed reactor 2.

In the fluidized bed reaction apparatus 11, as the fluidized bed reactor 2, a reactor for a vertical fluidized bed having an inner diameter of 21.4 mm and a height of 600 mm made of stainless steel (SUS316) was used, a SUS316 insertion tube having a diameter of 3.1 mm was introduced to the center of the reactor, a type K thermocouple was inserted to the insertion tube, and the temperature in the reactor was measured. Further, a grating and glass wool were disposed at a height of 100 mm from the lower portion of the fluidized bed reactor 2, and a solid reactant was packed thereon to form a solid reactant layer 3. The interior of the fluidized bed reactor 2 was heated by an electric furnace 2a.

A preheating mixer 4 was connected to the lower portion of the fluidized bed reactor 2 via a material gas supply line 5. The material gas supply line 5 and the preheating mixer 4 were respectively heated to 100° C. by a ribbon heater. The apparatus was so constituted that HFC-134a and nitrogen as a diluent gas were mixed while their flow rates were adjusted respectively by mass flow controllers 6a and 7a provided to a HFC-134a supply line 6 and a diluent gas supply line 7, and the gas mixture was supplied to the preheating mixer 4 through a gas mixture supply line 12. The outlet gas containing a reaction product was continuously withdrawn from the upper portion of the fluidized bed reactor 2, made to flow through a hydrogen fluoride trapping tube 10 packed with 28 g of 1/16 inch sodium fluoride pellets, collected in a sampling bag made of polyvinylidene fluoride (PVdF) (hereinafter referred to as PVdF bag), and subjected to composition analysis by means of gas chromatography (GC).

Further, the differential pressure measuring device was constituted as follows. That is, between an inlet side piping connected to the lower portion of the fluidized bed reactor 2 and an outlet side piping connected to the upper portion, a semitransparent PFA tube 13a having an inner diameter of 4.35 mm, processed into a U-shape having a height of 600 mm in a vertical direction was inserted, and a fluorine oil (density: 1.85 g/mL (25° C.)) was introduced to the tube to a height of 300 mm, thereby to constitute a differential pressure gauge 13.

(Fluidization Visualized Test Apparatus)

In the fluidized bed reaction apparatus 1 shown in FIG. 1, a visualized tester 14 having the same inner diameter and height (inner diameter: 21.4 mm×height: 600 mm) as the fluidized bed reactor 2, made of a transparent acrylic resin so that the flow state in the interior was visible, was disposed to constitute a fluidization visualized test apparatus 15. In the visualized tester 14, in the same manner as in the fluidized bed reactor 2 of the fluidized bed reaction apparatus 1, a grating and glass wool were disposed at a height of 100 mm from the lower portion, and a solid reactant was packed thereon to form a solid reactant layer 3. Further, to the lower portion of the visualized tester 14, a gas mixture supply line 12 to supply a gas mixture of HFC-134a and a diluent gas was connected. HFC-134a and nitrogen were mixed while their flow rates were adjusted by mass flow controllers 6a and 7a disposed to a HFC-134a supply line 6 and a diluent gas supply line 7, and the gas mixture is supplied to the visualized tester 14 by the mixed gas supply line 12.

Further, a differential pressure measuring device was provided so as to measure the differential pressure between on the inlet side on the outlet side of the visualized tester 14. That is, a differential pressure gauge 13 was provided in the same manner as the fluidized bed reaction apparatus 11 shown in FIG. 2, between an inlet side piping connected to the lower portion of the visualized tester 14 and an outlet side piping connected to the upper portion.

(Linear Velocity)

The linear velocity of each of a nitrogen gas and a gas mixture of nitrogen and HFC-134a was obtained by dividing the flow rate (volume flow rate) per unit time of each gas at the reaction temperature under the reaction pressure by the cross section area of the fluidized bed reactor 2 or the visualized tester 14.

Reactant Packing Example 1

The visualized tester of the fluidization visualized test apparatus was packed with 55 g of particulate potassium carbonate (manufactured by Asahi Glass Company, Limited, tradename: potassium carbonate FG, average particle size: 300 μm, bulk density: 0.9 g/cm$^3$, specific surface area: 1.2 m$^2$/g (hereinafter referred to as potassium carbonate FG)) as a solid reactant to a height of 150 mm.

Reactant Packing Example 2

The fluidized bed reactor of the fluidized bed reaction apparatus 11 was packed with 55 g of particulate potassium carbonate FG to a height of 150 mm.

Reactant Packing Example 3

The visualized tester of the fluidization visualized test apparatus was packed with 24 g of particulate potassium carbonate (manufactured by Asahi Glass Company, Limited, tradename: potassium carbonate FG R-10, average particle size: 10 μm, bulk density: 0.3 g/cm$^3$, specific surface area: 1.4 m$^2$/g (hereinafter referred to as potassium carbonate FG R-10)) to a height of 150 mm.

Reactant Packing Example 4

The fluidized bed reactor of the fluidized bed reaction apparatus 11 was packed with 24 g of particulate potassium carbonate FG R-10 to a height of 150 mm.

Fluidization Example 1

Through the fluidization visualized test apparatus packed with the solid reactant (potassium carbonate FG having an average particle size of 300 μm) shown in Reactant Packing Example 1, a nitrogen gas was made to flow at a flow rate of 151 mmol/min (linear velocity of 17 cm/s) at room temperature (25° C.) under normal pressure. On that occasion, the differential pressure between on the inlet side and on the outlet side of the visualized tester measured by the differential pressure gauge was 1,960 Pa. Further, in the visualized tester, mixing of an upper portion and a lower portion was observed in the entire layer of the solid reactant. That is, a completely fluidized state was visually confirmed.

Here, the fluidized state by visual observation of the solid reactant layer in the visualized tester was evaluated under the following standards.

◯: The upper portion and the lower portion are mixed in the entire layer of the solid reactant packed (completely fluidized state).

Δ: The upper portion and the lower portion are mixed only in a part of the layer of the solid reactant packed (partially fluidized state).

×: The upper portion and the lower portion of the layer of the solid reactant packed are not mixed (non-fluidized state).

Then, the flow rate of the nitrogen gas was gradually decreased, and the differential pressure between on the inlet side and on the outlet side of the visualized tester was measured by the differential pressure gauge at each flow rate, and the fluidized state of the solid reactant in the visualized tester was visually examined. The flow rate of the nitrogen gas, the linear velocity, the differential pressure and the fluidized state of the solid reactant visually observed are shown in Table 1. Further, a graph obtained by plotting the differential pressure relative to the linear velocity of the nitrogen gas is shown in FIG. 4.

In the graph obtained by plotting the differential pressure relative to the linear velocity of the gas, the inflection point at which the gradient of the graph changes is taken as the starting point of fluidization of the solid reactant layer, and the linear velocity at the inflection point may be taken as the fluidization starting velocity. Further, in a graph having two inflection points in the differential pressure, the linear velocity at an inflection point on the lower linear velocity side is taken as the partial fluidization starting velocity, and the linear velocity at an inflection point on the higher linear velocity side is taken as the complete fluidization starting velocity. It can be judged from Table 1 and FIG. 4 that in Fluidization Example 1, the partial fluidization starting velocity of the solid reactant layer is from 3 to 6 cm/s, and the complete fluidization starting velocity is 13 cm/s.

TABLE 1

| | | Fluidization Example 1 | | | | | | | |
|---|---|---|---|---|---|---|---|---|---|
| Temp. ° C. | | 25 | | | | | | | |
| Gas composition ratio | HFC-134a mol % | 0 | | | | | | | |
| | Nitrogen mol % | 100 | | | | | | | |
| Flow rate | HFC-134a mmol/min | 0 | 0 | 0 | 0 | 0 | 0 | 0 | 0 |
| | Nitrogen mmol/min | 151 | 142 | 134 | 125 | 116 | 107 | 98 | 89 |
| Linear velocity cm/s | | 17 | 16 | 15 | 14 | 13 | 12 | 11 | 10 |
| Differential pressure Pa | | 1960 | 1942 | 1905 | 1887 | 1869 | 1833 | 1760 | 1706 |
| Fluidized state by visual observation | | ○ | ○ | ○ | ○ | ○ | Δ | Δ | Δ |

| | | Fluidization Example 1 | | | | | | | |
|---|---|---|---|---|---|---|---|---|---|
| Temp. ° C. | | 25 | | | | | | | |
| Gas composition ratio | HFC-134a mol % | 0 | | | | | | | |
| | Nitrogen mol % | 100 | | | | | | | |
| Flow rate | HFC-134a mmol/min | 0 | 0 | 0 | 0 | 0 | 0 | 0 | 0 |
| | Nitrogen mmol/min | 80 | 71 | 62 | 53 | 44 | 35 | 27 | 18 |
| Linear velocity cm/s | | 9 | 8 | 7 | 6 | 5 | 4 | 3 | 2 |
| Differential pressure Pa | | 1669 | 1615 | 1542 | 1397 | 1252 | 1071 | 853 | 617 |
| Fluidized state by visual observation | | Δ | Δ | Δ | Δ | Δ | Δ | Δ | x |

Fluidization Example 2

Through the fluidization visualized test apparatus packed with the solid reactant (potassium carbonate FG) shown in Reactant Packing Example 1, a nitrogen gas at a flow rate of 121 mmol/min and HFC-134a at a flow rate of 30 mmol/min were mixed at room temperature (25° C.) under normal pressure and made to flow. That is, 80 mol % of a nitrogen gas and 20 mol % of HFC-134a were mixed and made to flow (linear velocity of gas mixture of 17 cm/s). On that occasion, the differential pressure between on the inlet side and on the outlet side of the visualized tester measured by the differential pressure gauge, and the fluidized state of the solid reactant in the visualized tester was visually examined. The flow rate of the nitrogen gas, the flow rate of HFC-134a, the linear velocity of the gas mixture, the differential pressure, and the fluidized state of the solid reactant visually observed are shown in Table 2. Further, a graph obtained by plotting the differential pressure relative to the linear velocity of the gas mixture is shown in FIG. 5. It can be judged from Table 2 and FIG. 5 that in Fluidization Example 2, the partial fluidization starting velocity of the solid reactant layer is from 4 to 8 cm/s, and the complete fluidization starting velocity is 15 cm/s.

TABLE 2

| | | Fluidization Example 2 | | | | | | | |
|---|---|---|---|---|---|---|---|---|---|
| Temp. ° C. | | 25 | | | | | | | |
| Gas composition ratio | HFC-134a mol % | 20 | | | | | | | |
| | Nitrogen mol % | 80 | | | | | | | |
| Flow rate | HFC-134a mmol/min | 30 | 29 | 27 | 25 | 23 | 21 | 20 | 18 |
| | Nitrogen mmol/min | 121 | 114 | 107 | 100 | 93 | 86 | 78 | 71 |
| Linear velocity cm/s | | 17 | 16 | 15 | 14 | 13 | 12 | 11 | 10 |
| Differential pressure Pa | | 2395 | 2341 | 2286 | 2177 | 2105 | 2032 | 1960 | 1887 |
| Fluidized state by visual observation | | ○ | ○ | ○ | Δ | Δ | Δ | Δ | Δ |

| | | Fluidization Example 2 | | | | | | | |
|---|---|---|---|---|---|---|---|---|---|
| Temp. ° C. | | 25 | | | | | | | |
| Gas composition ratio | HFC-134a mol % | 20 | | | | | | | |
| | Nitrogen mol % | 80 | | | | | | | |
| Flow rate | HFC-134a mmol/min | 16 | 14 | 12 | 11 | 9 | 7 | 5 | 4 |
| | Nitrogen mmol/min | 64 | 57 | 50 | 43 | 36 | 28 | 21 | 14 |
| Linear velocity cm/s | | 9 | 8 | 7 | 6 | 5 | 4 | 3 | 2 |
| Differential pressure Pa | | 1815 | 1724 | 1597 | 1433 | 1252 | 1034 | 835 | 581 |
| Fluidized state by visual observation | | Δ | Δ | Δ | Δ | Δ | Δ | x | x | the differential pressure gauge was 2,395 Pa. Further, in the visualized tester, mixing of an upper portion and a lower portion was observed in the entire layer of the solid reactant, and a completely fluidized state was visually confirmed.

Then, while the composition of HFC-134a and nitrogen (HFC-134a: $N_2$=20:80 (by mol %)) was kept, the nitrogen gas flow rate and the HFC-134a flow rate were gradually decreased, and at each flow rate, the differential pressure between on the inlet side and on the outlet side of the Fluidization Example 3

Through the fluidized bed reaction apparatus packed with the solid reactant (potassium carbonate FG) shown in Reactant Packing Example 2, a nitrogen gas was made to flow at a flow rate of 152 mmol/min (linear velocity of 17 cm/s) at room temperature (25° C.) under normal pressure. On that occasion, the differential pressure between on the inlet side and on the outlet side of the fluidized bed reactor measured by the differential pressure gauge was 2,631 Pa.

Figure 6:
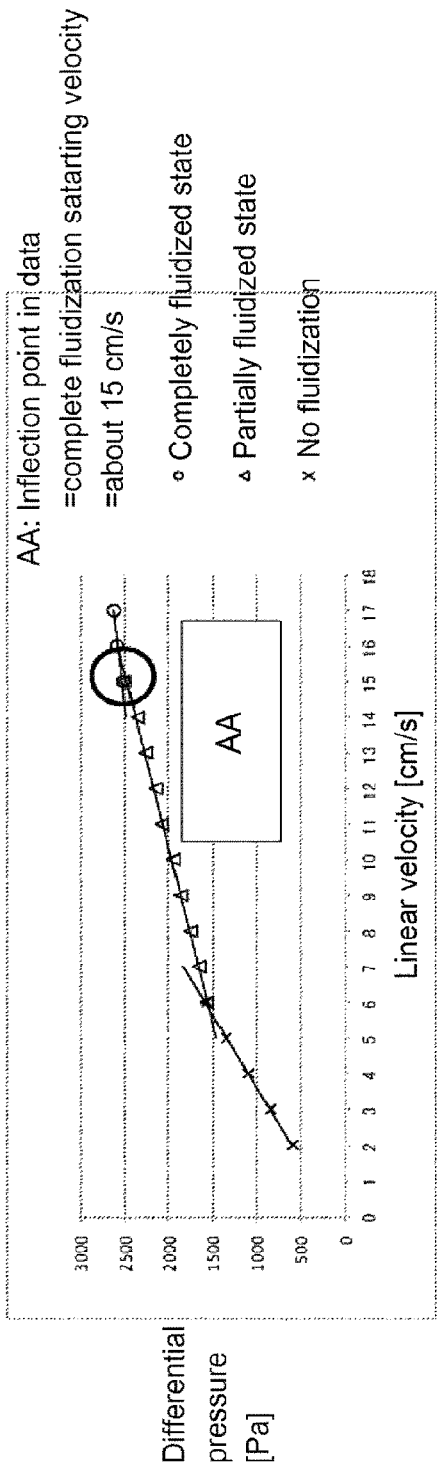
FIG. 6 is a graph obtained by plotting a differential pressure relative to a linear velocity of a nitrogen gas in Fluidization Example 3.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 3. Further, a graph obtained by plotting the differential pressure relative to the linear velocity of the nitrogen gas is shown in FIG. 6. It can be judged from Table 3 and FIG. 6 that in Fluidization Example 3, the partial fluidization starting velocity of the solid reactant layer is 6 cm/s, and the complete fluidization starting velocity is 15 cm/s.

TABLE 3

| | | Fluidization Example 3 | | | | | | | |
|---|---|---|---|---|---|---|---|---|---|
| Temp. ° C. | | 25 | | | | | | | |
| Gas composition ratio | HFC-134a mol % | 0 | | | | | | | |
| | Nitrogen mol % | 100 | | | | | | | |
| Flow rate | HFC-134a mmol/min | 0 | 0 | 0 | 0 | 0 | 0 | 0 | 0 |
| | Nitrogen mmol/min | 152 | 143 | 134 | 125 | 116 | 107 | 98 | 89 |
| Linear velocity cm/s | | 17 | 16 | 15 | 14 | 13 | 12 | 11 | 10 |
| Differential pressure Pa | | 2631 | 2595 | 2522 | 2359 | 2268 | 2159 | 2087 | 1960 |
| Fluidized state by visual observation | | — | — | — | — | — | — | — | — |

| | | Fluidization Example 3 | | | | | | | |
|---|---|---|---|---|---|---|---|---|---|
| Temp. ° C. | | 25 | | | | | | | |
| Gas composition ratio | HFC-134a mol % | 0 | | | | | | | |
| | Nitrogen mol % | 100 | | | | | | | |
| Flow rate | HFC-134a mmol/min | 0 | 0 | 0 | 0 | 0 | 0 | 0 | 0 |
| | Nitrogen mmol/min | 80 | 71 | 62 | 53 | 44 | 35 | 27 | 18 |
| Linear velocity cm/s | | 9 | 8 | 7 | 6 | 5 | 4 | 3 | 2 |
| Differential pressure Pa | | 1869 | 1760 | 1669 | 1579 | 1361 | 1107 | 853 | 599 |
| Fluidized state by visual observation | | — | — | — | — | — | — | — | — |

Fluidization Example 4

Through the fluidized bed reaction apparatus packed with the solid reactant shown in Reactant Packing Example 2, a nitrogen gas at a flow rate of 143 mmol/min and HFC-134a at a flow rate of 36 mmol/min were mixed at room temperature (25° C.) under normal pressure and made to flow. That is, 80 mol % of a nitrogen gas and 20 mol % of HFC-134a were mixed and made to flow (linear velocity of gas mixture of 20 cm/s). On that occasion, the differential pressure between on the inlet side and on the outlet side of the fluidized bed reactor measured by the differential pressure gauge was 3,248 Pa.

Figure 7:
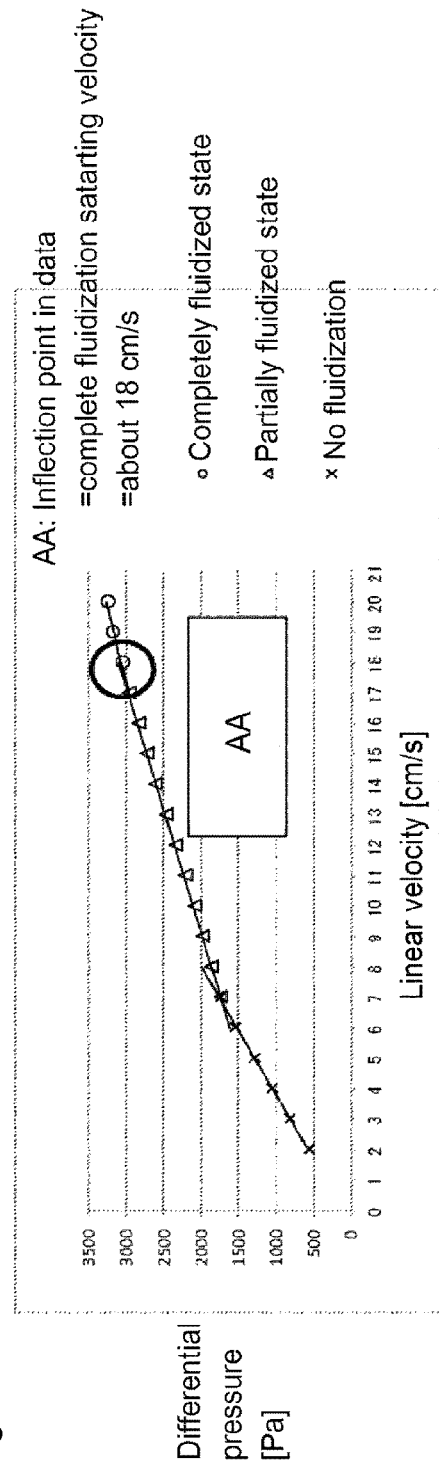
FIG. 7 is a graph obtained by plotting a differential pressure relative to a linear velocity of a gas mixture of HFC-134a and nitrogen in Fluidization Example 4.

Then, while the composition of HFC-134a and nitrogen (HFC-134a:$N_2$=20:80 (by mol %)) was kept, the nitrogen gas flow rate and the HFC-134a flow rate were gradually decreased, and at each flow rate, the differential pressure between on the inlet side and on the outlet side of the fluidized bed reactor was measured by the differential pressure gauge. The flow rate of the nitrogen gas, the flow rate of HFC-134a, the linear velocity of the gas mixture and the differential pressure are shown in Table 4. Further, a graph obtained by plotting the differential pressure relative to the linear velocity of the gas mixture is shown in FIG. 7. It can be judged from Table 4 and FIG. 7 that in Fluidization Example 4, the partial fluidization starting velocity of the solid reactant layer is 7 cm/s, and the complete fluidization starting velocity is 18 cm/s.

TABLE 4

| | | Fluidization Example 4 | | | | | | | | | |
|---|---|---|---|---|---|---|---|---|---|---|---|
| Temp. ° C. | | 25 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 36 | 34 | 32 | 30 | 29 | 27 | 25 | 23 | 21 | 20 |
| | Nitrogen mmol/min | 143 | 136 | 129 | 122 | 114 | 107 | 100 | 93 | 86 | 78 |
| Linear velocity cm/s | | 20 | 19 | 18 | 17 | 16 | 15 | 14 | 13 | 12 | 11 |
| Differential pressure Pa | | 3248 | 3175 | 3048 | 2958 | 2831 | 2722 | 2613 | 2468 | 2341 | 2214 |
| Fluidized state by visual observation | | — | — | — | — | — | — | — | — | — | — |

| | | Fluidization Example 4 | | | | | | | | |
|---|---|---|---|---|---|---|---|---|---|---|
| Temp. ° C. | | 25 | | | | | | | | |
| Gas composition ratio | HFC-134a mol % | 0 | | | | | | | | |
| | Nitrogen mol % | 100 | | | | | | | | |
| Flow rate | HFC-134a mmol/min | 18 | 16 | 14 | 12 | 11 | 9 | 7 | 5 | 4 |
| | Nitrogen mmol/min | 71 | 64 | 57 | 50 | 43 | 36 | 28 | 21 | 14 |
| Linear velocity cm/s | | 10 | 9 | 8 | 7 | 6 | 5 | 4 | 3 | 2 |
| Differential pressure Pa | | 2087 | 1978 | 1869 | 1742 | 1542 | 1288 | 1052 | 817 | 563 |
| Fluidized state by visual observation | | — | — | — | — | — | — | — | — | — |

Fluidization Example 5

The interior of the fluidized bed reactor of the fluidized bed reaction apparatus packed with the solid reactant shown in Reactant Packing Example 2 was heated to 310° C. by an electric furnace. A nitrogen gas was made to flow through the apparatus at a flow rate of 91 mmol/min (linear velocity of 20 cm/s) under normal pressure. On that occasion, the differential pressure between on the inlet side and on the outlet side of the fluidized bed reactor measured by the differential pressure gauge was 2,558 Pa.

Figure 8:
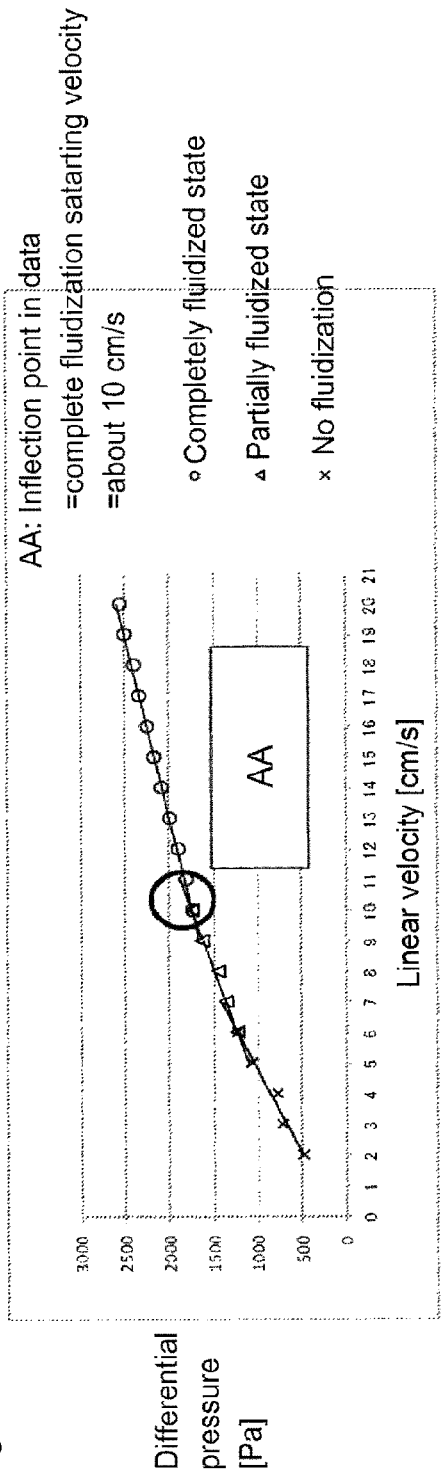
FIG. 8 is a graph obtained by plotting a differential pressure relative to a linear velocity of a nitrogen gas in Fluidization Example 5.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 5. Further, a graph obtained by plotting the differential pressure relative to the linear velocity of the nitrogen gas is shown in FIG. 8. It can be judged from Table 5 and FIG. 8 that in Fluidization Example 5, the partial fluidization starting velocity of the solid reactant layer is 6 cm/s, and the complete fluidization starting velocity is 10 cm/s.

TABLE 5

| | | Fluidization Example 5 | | | | | | | | | |
|---|---|---|---|---|---|---|---|---|---|---|---|
| Temp. ° C. | | 310 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | 0 |
| | Nitrogen mmol/min | 91 | 87 | 82 | 78 | 73 | 68 | 64 | 59 | 55 | 50 |
| Linear velocity cm/s | | 20 | 19 | 18 | 17 | 16 | 15 | 14 | 13 | 12 | 11 |
| Differential pressure Pa | | 2558 | 2504 | 2395 | 2341 | 2250 | 2177 | 2087 | 1996 | 1905 | 1815 |
| Fluidized state by visual observation | | — | — | — | — | — | — | — | — | — | — |

| | | Fluidization Example 5 | | | | | | | | |
|---|---|---|---|---|---|---|---|---|---|---|
| Temp. ° C. | | 310 | | | | | | | | |
| Gas composition ratio | HFC-134a mol % | 0 | | | | | | | | |
| | Nitrogen mol % | 100 | | | | | | | | |
| Flow rate | HFC-134a mmol/min | 0 | 0 | 0 | 0 | 0 | 0 | 0 | 0 | 0 |
| | Nitrogen mmol/min | 45 | 41 | 36 | 32 | 27 | 23 | 18 | 14 | 9 |
| Linear velocity cm/s | | 10 | 9 | 8 | 7 | 6 | 5 | 4 | 3 | 2 |
| Differential pressure Pa | | 1742 | 1633 | 1452 | 1361 | 1234 | 1071 | 780 | 726 | 490 |
| Fluidized state by visual observation | | — | — | — | — | — | — | — | — | — |

Fluidization Example 6

The interior of the fluidized bed reactor of the fluidized bed reaction apparatus packed with the solid reactant shown in Reactant Packing Example 2 was heated to 360° C. by an electric furnace. A nitrogen gas was made to flow through the apparatus at a flow rate of 84 mmol/min (linear velocity of 20 cm/s) under normal pressure. On that occasion, the differential pressure between on the inlet side and on the outlet side of the fluidized bed reactor measured by the differential pressure gauge was 2,431 Pa.

Figure 9:
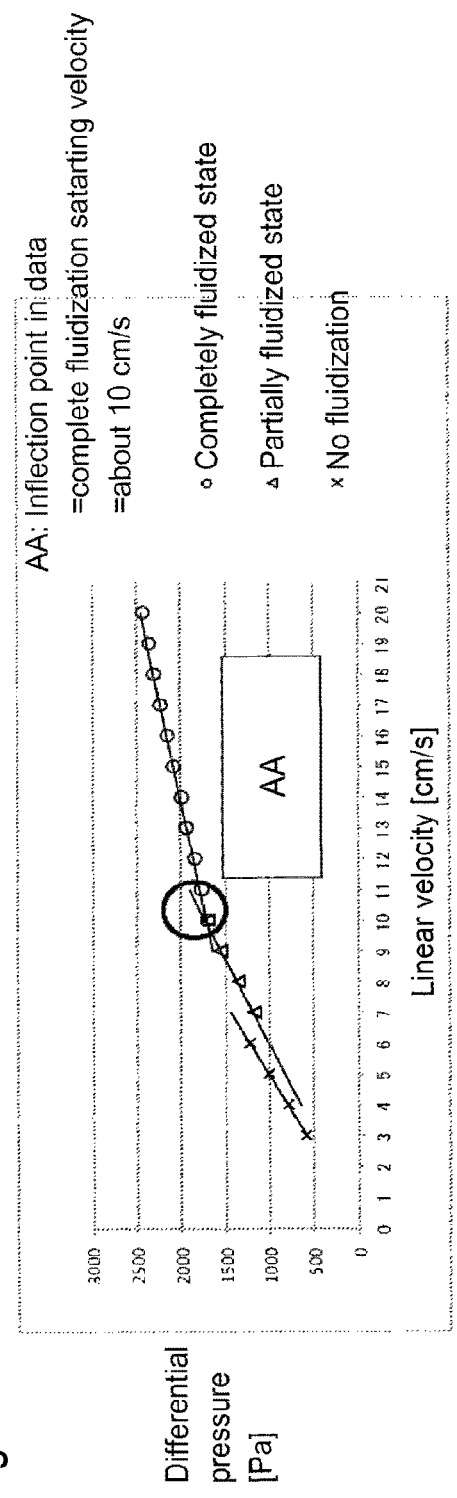
FIG. 9 is a graph obtained by plotting a differential pressure relative to a linear velocity of a nitrogen gas in Fluidization Example 6.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 6. Further, a graph obtained by plotting the differential pressure relative to the linear velocity of the nitrogen gas is shown in FIG. 9. It can be judged from Table 6 and FIG. 9 that in Fluidization Example 6, the partial fluidization starting velocity of the solid reactant layer is 7 cm/s, and the complete fluidization starting velocity is 10 cm/s.

TABLE 6

| | | Fluidization Example 6 | | | | | | | | | |
|---|---|---|---|---|---|---|---|---|---|---|---|
| Temp. ° C. | | 360 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | 0 |
| | Nitrogen mmol/min | 84 | 80 | 76 | 71 | 67 | 63 | 59 | 55 | 50 | 46 |

TABLE 6-continued

| Linear velocity cm/s | | 20 | 19 | 18 | 17 | 16 | 15 | 14 | 13 | 12 | 11 |
|---|---|---|---|---|---|---|---|---|---|---|---|
| Differential pressure Pa | | 2431 | 2359 | 2304 | 2232 | 2159 | 2087 | 1996 | 1942 | 1851 | 1778 |
| Fluidized state by visual observation | | — | — | — | — | — | — | — | — | — | — |

| | | Fluidization Example 6 | | | | | | | | | |
|---|---|---|---|---|---|---|---|---|---|---|---|
| Temp. ° C. | | | | | | 360 | | | | | |
| Gas composition ratio | HFC-134a mol % | | | | | 0 | | | | | |
| | Nitrogen mol % | | | | | 100 | | | | | |
| Flow rate | HFC-134a mmol/min | 0 | 0 | 0 | 0 | 0 | 0 | 0 | 0 | 0 | |
| | Nitrogen mmol/min | 42 | 38 | 33 | 29 | 25 | 21 | 17 | 12 | 8 | |
| Linear velocity cm/s | | 10 | 9 | 8 | 7 | 6 | 5 | 4 | 3 | 2 | |
| Differential pressure Pa | | 1706 | 1560 | 1361 | 1179 | 1234 | 1016 | 798 | 599 | 508 | |
| Fluidized state by visual observation | | — | — | — | — | — | — | — | — | — | |

Fluidization Example 7

The interior of the fluidized bed reactor of the fluidized bed reaction apparatus packed with the solid reactant shown in Reactant Packing Example 2 was heated to 410° C. by an electric furnace. A nitrogen gas was made to flow through the apparatus at a flow rate of 78 mmol/min (linear velocity of 20 cm/s) under normal pressure. On that occasion, the differential pressure between on the inlet side and on the outlet side of the fluidized bed reactor measured by the differential pressure gauge was 2,431 Pa.

Figure 10:
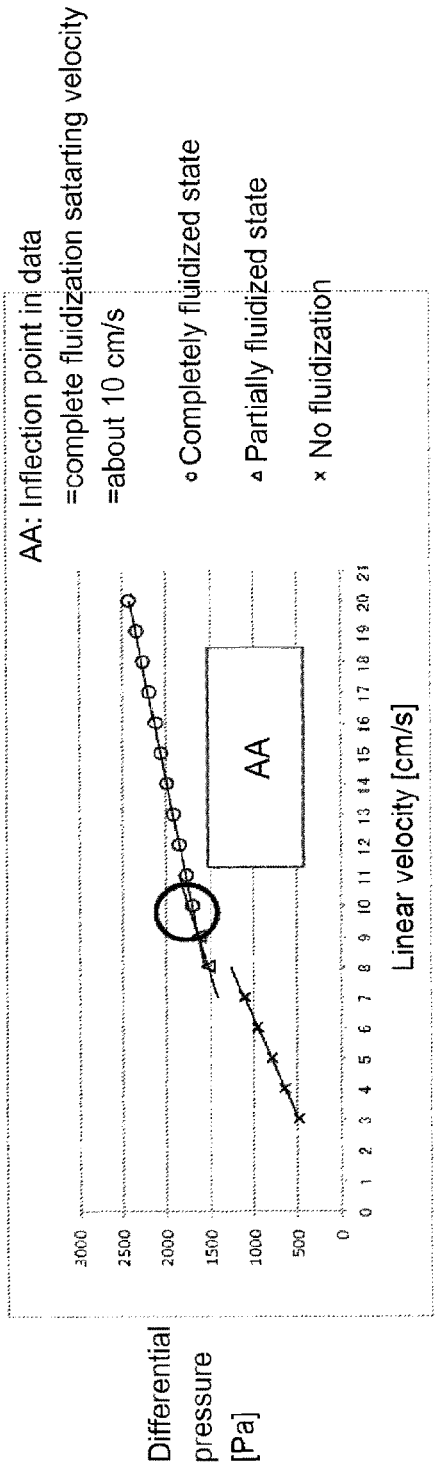
FIG. 10 is a graph obtained by plotting a differential pressure relative to a linear velocity of a nitrogen gas in Fluidization Example 7.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 7. Further, a graph obtained by plotting the differential pressure relative to the linear velocity of the nitrogen gas is shown in FIG. 10. It can be judged from Table 7 and FIG. 10 that in Fluidization Example 7, the partial fluidization starting velocity of the solid reactant layer is 8 cm/s, and the complete fluidization starting velocity is 10 cm/s.

Comparative Fluidization Example 1

Through the fluidization visualized test apparatus packed with the solid reactant (potassium carbonate FG R-10 having an average particle size of 10 μm) shown in Reactant Packing Example 3, a nitrogen gas was made to flow at a flow rate of 90 mmol/min (linear velocity of 10 cm/s) at room temperature (25° C.) under normal pressure. On that occasion, the differential pressure between on the inlet side and on the outlet side of the visualized tester measured by the differential pressure gauge was 4,990 Pa. Further, in the fluidized tester, mixing of an upper portion and a lower portion of the layer of the solid reactant was not confirmed, and the solid reactant layer formed a flow path and was in a single flow state. That is, the solid reactant layer was not fluidized.

Then, the nitrogen gas flow rate was gradually decreased, and at each flow rate, the differential pressure between on the inlet side and on the outlet side of the visualized tester was measured by the differential pressure gauge, and the fluidized state of the solid reactant in the visualized tester was visually examined. The flow rate of the nitrogen gas, the linear velocity, the differential pressure and the fluidized

TABLE 7

| | | Fluidization Example 7 | | | | | | | | |
|---|---|---|---|---|---|---|---|---|---|---|
| Temp. ° C. | | | | | | 410 | | | | |
| Gas composition ratio | HFC-134a mol % | | | | | 0 | | | | |
| | Nitrogen mol % | | | | | 100 | | | | |
| Flow rate | HFC-134a mmol/min | 0 | 0 | 0 | 0 | 0 | 0 | 0 | 0 | 0 |
| | Nitrogen mmol/min | 78 | 74 | 70 | 66 | 62 | 58 | 54 | 51 | 47 |
| Linear velocity cm/s | | 20 | 19 | 18 | 17 | 16 | 15 | 14 | 13 | 12 |
| Differential pressure Pa | | 2431 | 2341 | 2268 | 2196 | 2123 | 2069 | 1996 | 1923 | 1851 |
| Fluidized state by visual observation | | — | — | — | — | — | — | — | — | — |

Figure 11:
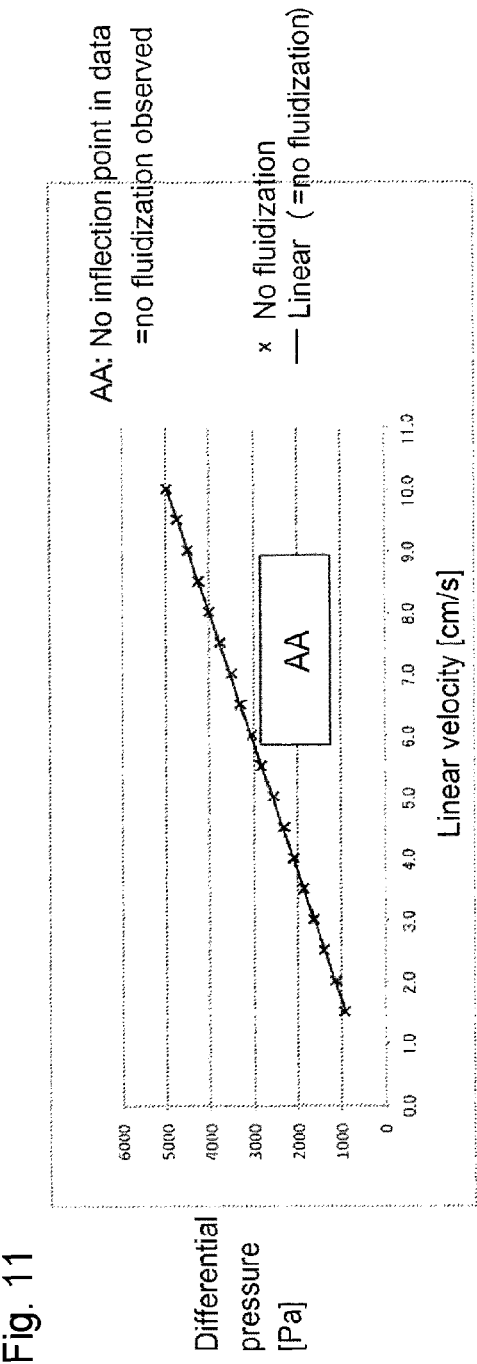
FIG. 11 is a graph obtained by plotting a differential pressure relative to a linear velocity of a nitrogen gas in Comparative Fluidization Example 1.

| | | Fluidization Example 7 | | | | | | | | |
|---|---|---|---|---|---|---|---|---|---|---|
| Temp. ° C. | | | | | | 410 | | | | |
| Gas composition ratio | HFC-134a mol % | | | | | 0 | | | | |
| | Nitrogen mol % | | | | | 100 | | | | |
| Flow rate | HFC-134a mmol/min | 0 | 0 | 0 | 0 | 0 | 0 | 0 | 0 | 0 |
| | Nitrogen mmol/min | 43 | 39 | 35 | 31 | 27 | 23 | 19 | 15 | 12 |
| Linear velocity cm/s | | 11 | 10 | 9 | 8 | 7 | 6 | 5 | 4 | 3 |
| Differential pressure Pa | | 1778 | 1706 | 1633 | 1524 | 1107 | 962 | 798 | 653 | 490 |
| Fluidized state by visual observation | | — | — | — | — | — | — | — | — | — | state of the solid reactant by visual observation are shown in Table 8. Further, a graph obtained by plotting the differential pressure relative to the linear velocity of the nitrogen gas is shown in FIG. 11. In the graph shown in FIG. 11, no inflection point of the differential pressure indicating the start of fluidization of the solid reactant layer was observed. It can be judged from Table 8 and FIG. 11 that in Comparative Fluidization Example 1, within a range of the linear velocity of at most 10 cm/s, no fluidization including partial fluidization occurred.

TABLE 8

| | | Comparative Fluidization Example 1 | | | | | | | | |
|---|---|---|---|---|---|---|---|---|---|---|
| Temp. ° C. | | 25 | | | | | | | | |
| Gas composition ratio | HFC-134a mol % | 0 | | | | | | | | |
| | Nitrogen mol % | 100 | | | | | | | | |
| Flow rate | HFC-134a mmol/min | 0 | 0 | 0 | 0 | 0 | 0 | 0 | 0 | 0 |
| | Nitrogen mmol/min | 90 | 86 | 81 | 77 | 72 | 67 | 63 | 58 | 54 |
| Linear velocity cm/s | | 10.0 | 9.5 | 9.0 | 8.5 | 8.0 | 7.5 | 7.0 | 6.5 | 6.0 |
| Differential pressure Pa | | 4990 | 4754 | 4500 | 4264 | 4028 | 3774 | 3502 | 3302 | 3048 |
| Fluidized state by visual observation | | x | x | x | x | x | x | x | x | x |
| | | Comparative Fluidization Example 1 | | | | | | | | |
| Temp. ° C. | | 25 | | | | | | | | |
| Gas composition ratio | HFC-134a mol % | 0 | | | | | | | | |
| | Nitrogen mol % | 100 | | | | | | | | |
| Flow rate | HFC-134a mmol/min | 0 | 0 | 0 | 0 | 0 | 0 | 0 | 0 | 0 |
| | Nitrogen mmol/min | 49 | 45 | 40 | 36 | 31 | 27 | 22 | 18 | 13 |
| Linear velocity cm/s | | 5.5 | 5.0 | 4.5 | 4.0 | 3.5 | 3.0 | 2.5 | 2.0 | 1.5 |
| Differential pressure Pa | | 2831 | 2558 | 2323 | 2105 | 1869 | 1651 | 1415 | 1143 | 944 |
| Fluidized state by visual observation | | x | x | x | x | x | x | x | x | x |

Comparative Fluidization Example 2

Through the fluidized bed reaction apparatus packed with the solid reactant (potassium carbonate FG R-10) shown in Reactant Packing Example 4, a nitrogen gas was made to flow at a flow rate of 89 mmol/min (linear velocity of 10 cm/s) at room temperature (25° C.) under normal pressure. On that occasion, the differential pressure between on the inlet side and on the outlet side of the fluidized bed reactor measured by the differential pressure gauge was 1,942 Pa.

Figure 12:
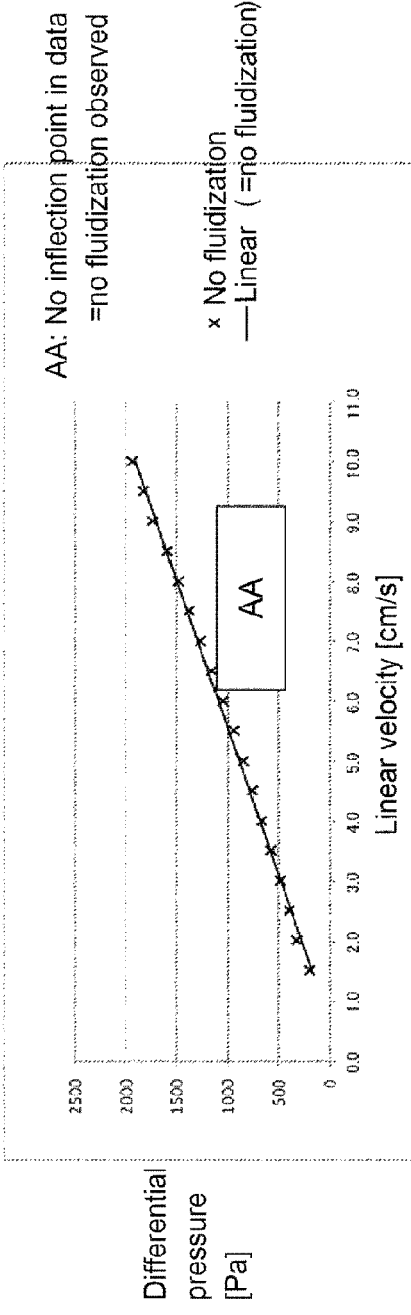
FIG. 12 is a graph obtained by plotting a differential pressure relative to a linear velocity of a nitrogen gas in Comparative Fluidization Example 2.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 9. Further, a graph obtained by plotting the differential pressure relative to the linear velocity of the nitrogen gas is shown in FIG. 12. In the graph shown in FIG. 12, no inflection point of the differential pressure indicating the start of fluidization of the solid reactant layer was observed. It can be judged from Table 9 and FIG. 12 that in Comparative Fluidization Example 2, within a range of the linear velocity of at most 10 cm/s, no fluidization including partial fluidization occurred.

TABLE 9

| | | Comparative Fluidization Example 2 | | | | | | | | |
|---|---|---|---|---|---|---|---|---|---|---|
| Temp. ° C. | | 25 | | | | | | | | |
| Gas composition ratio | HFC-134a mol % | 0 | | | | | | | | |
| | Nitrogen mol % | 100 | | | | | | | | |
| Flow rate | HFC-134a mmol/min | 0 | 0 | 0 | 0 | 0 | 0 | 0 | 0 | 0 |
| | Nitrogen mmol/min | 89 | 85 | 80 | 76 | 71 | 67 | 62 | 58 | 53 |
| Linear velocity cm/s | | 10.0 | 9.5 | 9.0 | 8.5 | 8.0 | 7.5 | 7.0 | 6.5 | 6.0 |
| Differential pressure Pa | | 1942 | 1833 | 1742 | 1597 | 1488 | 1379 | 1270 | 1161 | 1052 |
| Fluidized state by visual observation | | — | — | — | — | — | — | — | — | — |

TABLE 9-continued

| | | Comparative Fluidization Example 2 | | | | | | | | |
|---|---|---|---|---|---|---|---|---|---|---|
| Temp. ° C. | | 25 | | | | | | | | |
| Gas composition ratio | HFC-134a mol % | 0 | | | | | | | | |
| | Nitrogen mol % | 100 | | | | | | | | |
| Flow rate | HFC-134a mmol/min | 0 | 0 | 0 | 0 | 0 | 0 | 0 | 0 | 0 |
| | Nitrogen mmol/min | 49 | 44 | 40 | 35 | 31 | 27 | 22 | 18 | 13 |
| Linear velocity cm/s | | 5.5 | 5.0 | 4.5 | 4.0 | 3.5 | 3.0 | 2.5 | 2.0 | 1.5 |
| Differential pressure Pa | | 944 | 853 | 762 | 671 | 581 | 490 | 399 | 327 | 200 |
| Fluidized state by visual observation | | — | — | — | — | — | — | — | — | — |

Comparative Fluidization Example 3

The interior of the fluidized bed reactor of the fluidized bed reaction apparatus packed with the solid reactant shown in Reactant Packing Example 4 was heated to 310° C. by an electric furnace. A nitrogen gas was made to flow through the apparatus at a flow rate of 89 mmol/min (linear velocity of 8.5 cm/s) under normal pressure. On that occasion, the differential pressure between on the inlet side and on the outlet side of the fluidized bed reactor measured by the differential pressure gauge was 1,688 Pa.

Figure 13:
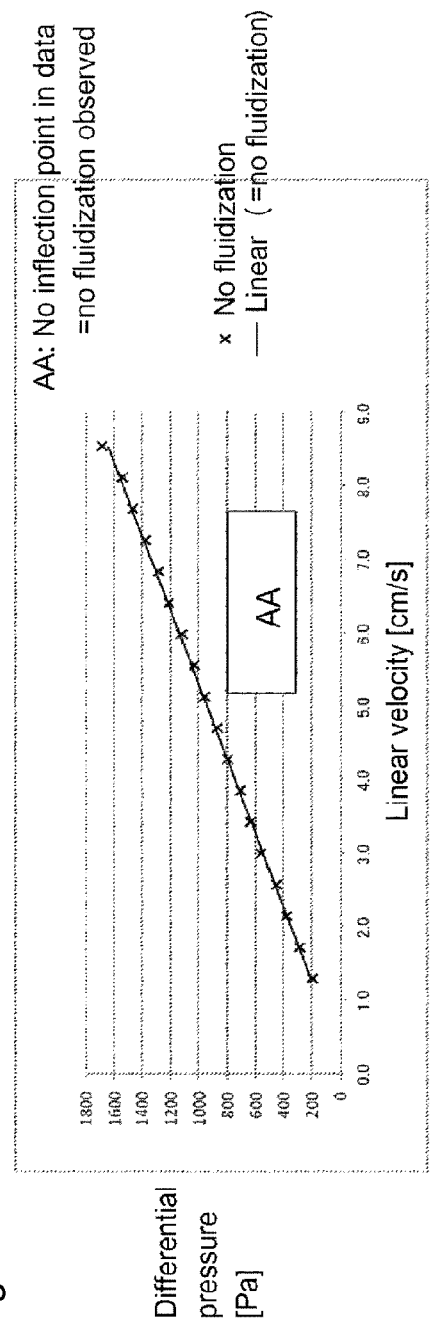
FIG. 13 is a graph obtained by plotting a differential pressure relative to a linear velocity of a nitrogen gas in Comparative Fluidization Example 3.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 10. Further, a graph obtained by plotting the differential pressure relative to the linear velocity of the nitrogen gas is shown in FIG. 13. In the graph shown in FIG. 13, no inflection point in the differential pressure indicating the start of fluidization of the solid reactant layer was observed. It can be judged from Table 10 and FIG. 13 that in Comparative Fluidization Example 3, within a range of the linear velocity of at most 8.5 cm/s, no fluidization including partial fluidization occurred.

Comparative Fluidization Example 4

The interior of the fluidized bed reactor of the fluidized bed reaction apparatus packed with the solid reactant shown in Reactant Packing Example 4 was heated to 360° C. by an electric furnace. A nitrogen gas was made to flow through the apparatus at a flow rate of 36 mmol/min (linear velocity of 8.5 cm/s) under normal pressure. On that occasion, the differential pressure between on the inlet side and on the outlet side of the fluidized bed reactor measured by the differential pressure gauge was 2,087 Pa.

Figure 14:
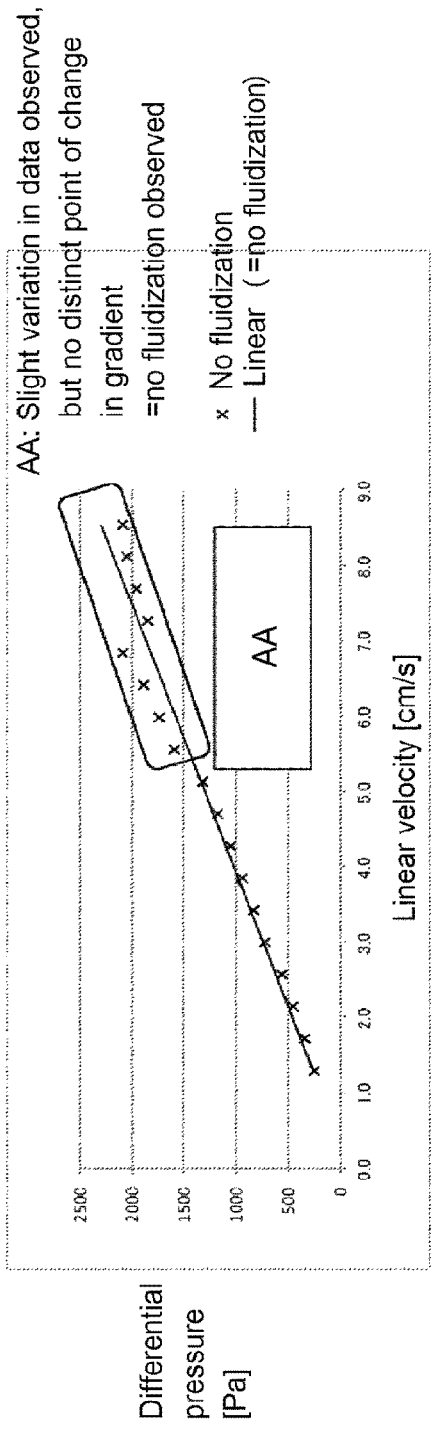
FIG. 14 is a graph obtained by plotting a differential pressure relative to a linear velocity of a nitrogen gas in Comparative Fluidization Example 4.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 11. Further, a graph obtained by plotting the differential pressure relative to the linear velocity of the nitrogen gas is shown in FIG. 14. In the graph shown in FIG. 14, no inflection point in the differential pressure indicating the start of fluidization of the solid reactant layer was observed. It can be judged from Table 11 and FIG. 14 that in Comparative Fluidization Example 4, within a range of the linear velocity of at most 8.5 cm/s, no fluidization including partial fluidization occurred.

TABLE 10

| | | Comparative Fluidization Example 3 | | | | | | | | | |
|---|---|---|---|---|---|---|---|---|---|---|---|
| Temp. ° C. | | 310 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | 0 |
| | Nitrogen mmol/min | 39 | 37 | 35 | 33 | 31 | 29 | 27 | 25 | 23 | 21 |
| Linear velocity cm/s | | 8.5 | 8.1 | 7.7 | 7.3 | 6.8 | 6.4 | 6.0 | 5.5 | 5.1 | 4.7 |
| Differential pressure Pa | | 1688 | 1542 | 1470 | 1379 | 1288 | 1216 | 1125 | 1034 | 962 | 871 |
| Fluidized state by visual observation | | — | — | — | — | — | — | — | — | — | — |
| | | Comparative Fluidization Example 3 | | | | | | | | | |
| Temp. ° C. | | 310 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | 0 |
| | Nitrogen mmol/min | 19 | 17 | 15 | 14 | 12 | 10 | 8 | 6 | 4 | 2 |
| Linear velocity cm/s | | 4.3 | 3.8 | 3.4 | 3.0 | 2.6 | 2.1 | 1.7 | 1.3 | 0.9 | 0.4 |
| Differential pressure Pa | | 798 | 708 | 635 | 563 | 454 | 381 | 290 | 200 | 127 | 73 |
| Fluidized state by visual observation | | — | — | — | — | — | — | — | — | — | — |

TABLE 11

| | | Comparative Fluidization Example 4 | | | | | | | | | |
|---|---|---|---|---|---|---|---|---|---|---|---|
| Temp. ° C. | | 360 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | 0 |
| | Nitrogen mmol/min | 36 | 34 | 32 | 30 | 29 | 27 | 25 | 23 | 21 | 20 |
| Linear velocity cm/s | | 8.5 | 8.1 | 7.7 | 7.3 | 6.8 | 6.4 | 6.0 | 5.5 | 5.1 | 4.7 |
| Differential pressure Pa | | 2087 | 2050 | 1960 | 1851 | 2087 | 1887 | 1742 | 1597 | 1325 | 1179 |
| Fluidized state by visual observation | | — | — | — | — | — | — | — | — | — | — |

| | | Comparative Fluidization Example 4 | | | | | | | | | |
|---|---|---|---|---|---|---|---|---|---|---|---|
| Temp. ° C. | | 360 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | |
| | Nitrogen mmol/min | 18 | 16 | 14 | 12 | 11 | 9 | 7 | 5 | 4 | 2 |
| Linear velocity cm/s | | 4.3 | 3.8 | 3.4 | 3.0 | 2.6 | 2.1 | 1.7 | 1.3 | 0.9 | 0.4 |
| Differential pressure Pa | | 1052 | 944 | 835 | 726 | 563 | 454 | 345 | 254 | 145.2 | 73 |
| Fluidized state by visual observation | | — | — | — | — | — | — | — | — | — | — |

Comparative Fluidization Example 5

The interior of the fluidized bed reactor of the fluidized bed reaction apparatus packed with the solid reactant shown in Reactant Packing Example 4 was heated to 410° C. by an electric furnace. A nitrogen gas was made to flow through the apparatus at a flow rate of 39 mmol/min (linear velocity of 10 cm/s) under normal pressure. On that occasion, the differential pressure between on the inlet side and on the outlet side of the fluidized bed reactor measured by the differential pressure gauge was 1,579 Pa.

Figure 15:
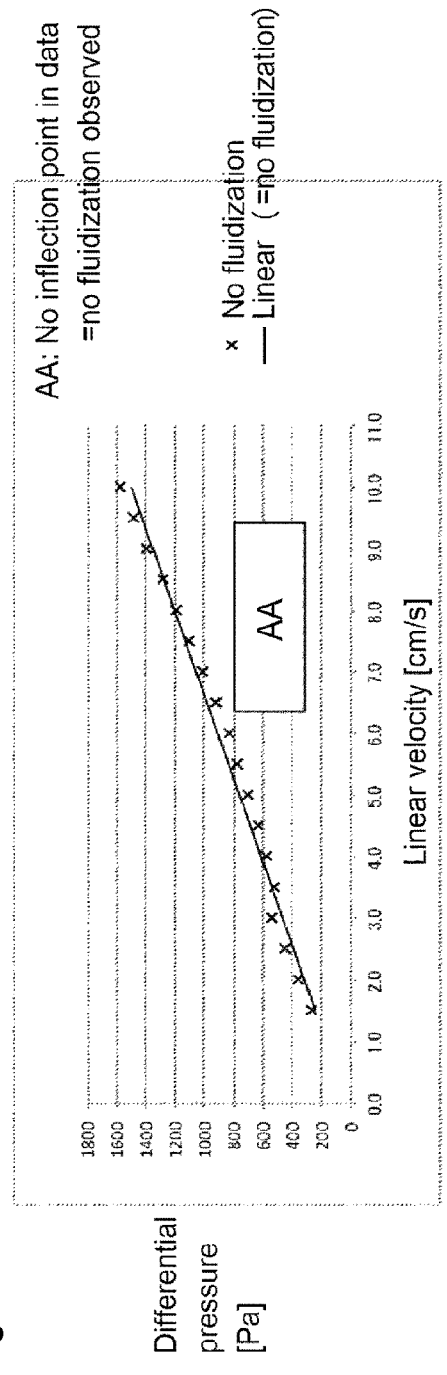
FIG. 15 is a graph obtained by plotting a differential pressure relative to a linear velocity of a nitrogen gas in Comparative Fluidization Example 5.

Then, the nitrogen gas flow rate was gradually decreased, and at each flow rate, the differential pressure between on the inlet side and on the outlet side of the fluidized bed reactor was measured by the differential pressure gauge. The flow rate of the nitrogen gas, the linear velocity and the differential pressure are shown in Table 12. Further, a graph obtained by plotting the differential pressure relative to the linear velocity of the nitrogen gas is shown in FIG. 15. In the graph shown in FIG. 15, no inflection point in the differential pressure indicating the start of fluidization of the solid reactant layer was observed. It can be judged from Table 12 and FIG. 15 that in Comparative Fluidization Example 5, within a range of the linear velocity of at most 10 cm/s, no fluidization including partial fluidization occurred.

TABLE 12

| | | Comparative Fluidization Example 5 | | | | | | | | | |
|---|---|---|---|---|---|---|---|---|---|---|---|
| Temp. ° C. | | 410 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | 0 |
| | Nitrogen mmol/min | 39 | 37 | 35 | 33 | 31 | 29 | 27 | 25 | 23 | 21 |
| Linear velocity cm/s | | 10.0 | 9.5 | 9.0 | 8.5 | 8.0 | 7.5 | 7.0 | 6.5 | 6.0 | 5.5 |
| Differential pressure Pa | | 1579 | 1488 | 1397 | 1288 | 1198 | 1107 | 1016 | 925 | 835 | 780 |
| Fluidized state by visual observation | | — | — | — | — | — | — | — | — | — | — |

| | | Comparative Fluidization Example 5 | | | | | | | | | |
|---|---|---|---|---|---|---|---|---|---|---|---|
| Temp. ° C. | | 410 | | | | | | | | | |
| Gas composition ratio | HFC-134a mol % | 0 | | | | | | | | | |
| | Nitrogen mol % | 100 | | | | | | | | | |
| Flow rate | HFC-134a mmol/min | 0 | 0 | 0 | 0 | 0 | 0 | 0 | 0 | 0 | |
| | Nitrogen mmol/min | 19 | 17 | 15 | 14 | 12 | 10 | 8 | 6 | 4 | 2 |
| Linear velocity cm/s | | 5.0 | 4.5 | 4.0 | 3.5 | 3.0 | 2.5 | 2.0 | 1.5 | 1.0 | 0.5 |
| Differential pressure Pa | | 708 | 635 | 581 | 526 | 544 | 454 | 363 | 272 | 145.2 | 54 |
| Fluidized state by visual observation | | — | — | — | — | — | — | — | — | — | — |

The results of the fluidization tests in the above Fluidization Examples 1 to 7 and Comparative Fluidization Examples 1 to 5 are shown in Table 13. It is found from Table 13 that potassium carbonate having an average particle size of 300 μm has favorable flowability, and it can be in a fluidized state by making a gas to flow therethrough at a predetermined linear velocity, however, potassium carbonate having an average particle size of 10 μm is poor in the flowability, and it is not fluidized at a linear velocity of from several cm/s to a dozen cm/s.

2.5 mmol/min. HFC-134a was made to flow and reacted for 10 minutes from the start of the flow of HFC-134a, and then only the supply of HFC-134a was terminated while the flow rate of the nitrogen gas was unchanged, to complete the reaction in Example 1. The outlet gas from 5 minutes after the start of the flow of HFC-134a to the completion of the reaction was continuously collected in a PVdF bag.

Then, after completion of the reaction in Example 1, without exchanging potassium carbonate in the fluidized bed reactor, Example 2 was carried out as it was. In Example 2,

TABLE 13

| | | Fluidization Example 1 | Fluidization Example 2 | Fluidization Example 3 | Fluidization Example 4 | Fluidization Example 5 | Fluidization Example 6 | Fluidization Example 7 |
|---|---|---|---|---|---|---|---|---|
| Reactant Packing Example | | Packing Example 1 | Packing Example 1 | Packing Example 2 | Packing Example 2 | Packing Example 2 | Packing Example 2 | Packing Example 2 |
| Average particle size of potassium carbonate μm | | 300 | 300 | 300 | 300 | 300 | 300 | 300 |
| Fluidization visualized test apparatus or fluidized bed reaction apparatus | | Fluidization visualized test apparatus | Fluidization visualized test apparatus | Fluidized bed reaction apparatus | Fluidized bed reaction apparatus | Fluidized bed reaction apparatus | Fluidized bed reaction apparatus | Fluidized bed reaction apparatus |
| Temperature ° C. | | 25 | 25 | 25 | 25 | 310 | 360 | 410 |
| Gas composition ratio | HFC-134a mol % | 0 | 20 | 0 | 20 | 0 | 0 | 0 |
| | Nitrogen mol % | 100 | 80 | 100 | 80 | 100 | 100 | 100 |
| Linear velocity/ differential pressure plot analysis | Partial fluidization starting velocity | 6 cm/s | 8 cm/s | 6 cm/s | 7 cm/s | 6 cm/s | 7 cm/s | 8 cm/s |
| | Complete fluidization starting velocity | 13 cm/s | 15 cm/s | 15 cm/s | 18 cm/s | 10 cm/s | 10 cm/s | 10 cm/s |
| Visual observation | Partial fluidization starting velocity | 3 cm/s | 4 cm/s | — | — | — | — | — |
| | Complete fluidization starting velocity | 13 cm/s | 15 cm/s | — | — | — | — | — |

| | | Comparative Fluidization Example 1 | Comparative Fluidization Example 2 | Comparative Fluidization Example 3 | Comparative Fluidization Example 4 | Comparative Fluidization Example 1 |
|---|---|---|---|---|---|---|
| Reactant Packing Example | | Packing Example 3 | Packing Example 4 | Packing Example 4 | Packing Example 4 | Packing Example 4 |
| Average particle size of potassium carbonate μm | | 10 | 10 | 10 | 10 | 10 |
| Fluidization visualized test apparatus or fluidized bed reaction apparatus | | Fluidization visualized test apparatus | Fluidized bed reaction apparatus | Fluidized bed reaction apparatus | Fluidized bed reaction apparatus | Fluidized bed reaction apparatus |
| Temperature ° C. | | 25 | 25 | 310 | 360 | 410 |
| Gas composition ratio | HFC-134a mol % | 0 | 0 | 0 | 0 | 0 |
| | Nitrogen mol % | 100 | 100 | 100 | 100 | 100 |
| Linear velocity/ differential pressure plot analysis | Partial fluidization starting velocity | No fluidization at less than 10 cm/s | No fluidization at less than 10 cm/s | No fluidization at less than 8.5 cm/s | No fluidization at less than 8.5 cm/s | No fluidization at less than 10 cm/s |
| | Complete fluidization starting velocity | | | | | |
| Visual observation | Partial fluidization starting velocity | No fluidization at less than 10 cm/s (single flow) | — | — | — | — |
| | Complete fluidization starting velocity | | | | | |

Examples 1 and 2

First, in Example 1, the interior of the fluidized bed reactor of the fluidized bed reaction apparatus packed with the solid reactant (potassium carbonate FG) shown in Reactant Packing Example 2 was heated by an electric furnace at 360° C. Then, a nitrogen gas was made to flow through the fluidized bed reaction apparatus at a flow rate of 50.3 mmol/min (linear velocity of 12 cm/s) under normal pressure. From the results of the fluidization test (Fluidization Example 6), it is considered that the layer of potassium carbonate FG was in a completely fluidized state at this linear velocity.

Then, while the flow rate of the nitrogen gas was kept, HFC-134a was started to be made to flow at a flow rate of HFC-134a was brought into contact with and reacted with the solid reactant in the same manner as in Example 1 except that the reaction conditions were as identified in Table 14. Further, the composition of the outlet gas collected in the PVdF bag was analyzed by gas chromatography (GC). The analysis results are shown in Table 14 together with the reaction conditions (the nitrogen flow rate before the reaction, the reaction temperature, the HFC-134a flow rate at the time of the reaction, the nitrogen flow rate at the time of the reaction, the composition at the time of the reaction (HFC-134a:nitrogen (molar ratio)), the linear velocity at the time of the reaction, the contact time at the time of the reaction, presence or absence of the fluidized state at the time of the reaction, and the time over which HFC-134a was made to flow (hereinafter referred to as the reaction time)).

Comparative Examples 1 and 2

First, in Comparative Example 1, while the interior of the fluidized bed reactor of the fluidized bed reaction apparatus packed with the solid reactant (potassium carbonate FG R-10) shown in Reactant Packing Example 4 was heated to 360° C. by an electric furnace, a nitrogen gas was made to flow through the fluidized bed reaction apparatus at a flow rate of 6.24 mmol/min (linear velocity of 1.5 cm/s) under normal pressure. From the results of the above fluidization test (Comparative Fluidization Example 4), it is considered that potassium carbonate FGR-10 was not fluidized at this linear velocity.

Then, while the flow rate of the nitrogen gas was kept, HFC-134a was started to be made to flow at a flow rate of 0.31 mmol/min. HFC-134a was made to flow and reacted for 15 minutes from the start of the flow of HFC-134a, and then only the supply of HFC-134a was terminated while the flow rate of the nitrogen gas was unchanged, to complete the reaction in Comparative Example 1. The outlet gas from 5 minutes after the start of the flow of HFC-134a to the completion of the reaction was continuously collected in a PVdF bag.

Then, after completion of the reaction in Comparative Example 1, without exchanging potassium carbonate in the fluidized bed reactor, Comparative Example 2 was conducted as it was. In Comparative Example 2, HFC-134a was brought into contact with and reacted with the solid reactant in the same manner as in Comparative Example 1 except that the reaction conditions were as identified in Table 15. And, the composition of the outlet gas collected in the PVdF bag was analyzed by gas chromatography (GC). The analysis results are shown in Table 15 together with the reaction conditions (the nitrogen flow rate before the reaction, the reaction temperature, the HFC-134a flow rate at the time of the reaction, the nitrogen flow rate at the time of the reaction, the composition at the time of the reaction (HFC-134a:nitrogen (molar ratio)), the linear velocity at the time of the reaction, the contact time at the time of the reaction, presence or absence of the fluidized state at the time of the reaction, and the reaction time).

Then, in Examples 1 and 2 and Comparative Examples 1 and 2, based on the area ratio (GC Area %) of the outlet gas obtained by gas chromatography analysis, the degree of conversion (reactivity) of HFC-134a, the selectivity for HFO-1123 and the selectivity for other gases were obtained as follows. In the following formulae, (HFC-134a) and (HFO-1123) respectively represent the area ratios (%) of (HFC-134a) and (HFO-1123) in the outlet gas.

The results are shown in the lower rows in Table 14 with respect to Examples 1 and 2 and in the lower rows in Table 15 with respect to Comparative Examples 1 and 2.

[Degree of Conversion (%) of HFC-134a]

It represents the proportion of components other than HFC-134a among components derived from HFC-134a in the outlet gas. It is calculated from {100−(HFC-134a)}/100×100(%) in the outlet gas.

[Selectivity (%) For HFO-1123]

It represents the proportion of HFC-134a converted to HFO-1123 based on the entire HFC-134a reacted, represented by %. It is calculated from (HFO-1123)/{100−(HFC-134a)}×100(%) in the outlet gas.

[Selectivity (%) For Other Gases]

It represents the proportion of HFC-134a converted to compounds other than HFO-1123 based on the entire HFC-134a reacted, represented by %. It is calculated from {100−(HFC-134a)−(HFO-1123)}/{100−(HFC-134a)}×100(%) in the outlet gas.

TABLE 14

| | | Example 1 | Example 2 |
|---|---|---|---|
| Solid reactant | | Potassium carbonate FG | |
| Reactant packing amount (g) | | 55 | |
| Reactant packing amount (mmol) | | 398 | |
| Nitrogen flow rate before reaction (mmol/min) | | 50.3 | 46.6 |
| Reaction temperature (° C.) | | 360 | 410 |
| HFC-134a flow rate at the time of reaction (mmol/min) | | 2.5 | 2.3 |
| Nitrogen flow rate at the time of reaction (mmol/min) | | 50.3 | 46.6 |
| Composition ratio at the time of reaction HFC-134a:N2 (molar ratio) | | 5:95 | 5:95 |
| Linear velocity at the time of reaction (cm/s) | | 12.0 | 12.0 |
| Compact time at the time of reaction (s) | | 1.25 | 1.25 |
| Fluidized state at the time of reaction | | Completely fluidized state | |
| Reaction time (min) | | 10 | 10 |
| Structure | Name | Outlet gas composition (other than nitrogen) (area %) | |
| CF2=CHF | HFO-1123 | 3.8 | 4.2 |
| CF3CH2F | HFC-134a | 96.0 | 95.6 |
| Others | | 0.2 | 0.2 |
| Degree of conversion of HFC-134a (%) | | 4.0 | 4.4 |
| Selectivity for HFO-1123 (%) | | 95.1 | 95.6 |
| Selectivity for other gases (%) | | 4.9 | 4.4 |

TABLE 15

| | | Comparative Example 1 | Comparative Example 2 |
|---|---|---|---|
| Solid reactant | | Potassium carbonate FG R-10 | |
| Reactant packing amount (g) | | 18 | |
| Reactant packing amount (mmol) | | 127 | |
| Nitrogen flow rate before reaction (mmol/min) | | 6.24 | 5.78 |
| Reaction temperature (° C.) | | 360 | 410 |
| HFC-134a flow rate at the time of reaction (mmol/min) | | 0.31 | 0.29 |
| Nitrogen flow rate at the time of reaction (mmol/min) | | 6.24 | 5.78 |
| Composition ratio at the time of reaction HFC-134a:N2 (molar ratio) | | 5:95 | 5:95 |
| Linear velocity at the time of reaction (cm/s) | | 1.5 | 1.5 |
| Compact time at the time of reaction (s) | | 10.00 | 10.00 |
| Fluidized state at the time of reaction | | No fluidization | |
| Reaction time (min) | | 15 | 15 |
| Structure | Name | Outlet gas composition (other than nitrogen) (area %) | |
| CF2=CHF | HFO-1123 | 5.0 | 5.8 |
| CF3CH2F | HFC-134a | 93.5 | 93.7 |
| Others | | 1.5 | 0.5 |
| Degree of conversion of HFC-134a (%) | | 6.5 | 6.3 |
| Selectivity for HFO-1123 (%) | | 76.4 | 91.6 |
| Selectivity for other gases (%) | | 23.6 | 8.4 |

B. Synthesis Reaction Using Calcium Oxide as Solid Reactant (Analysis Conditions)

The composition of the outlet gas was analyzed under the same conditions as in Example 1.

(Reaction Apparatus 2)

Figure 16:
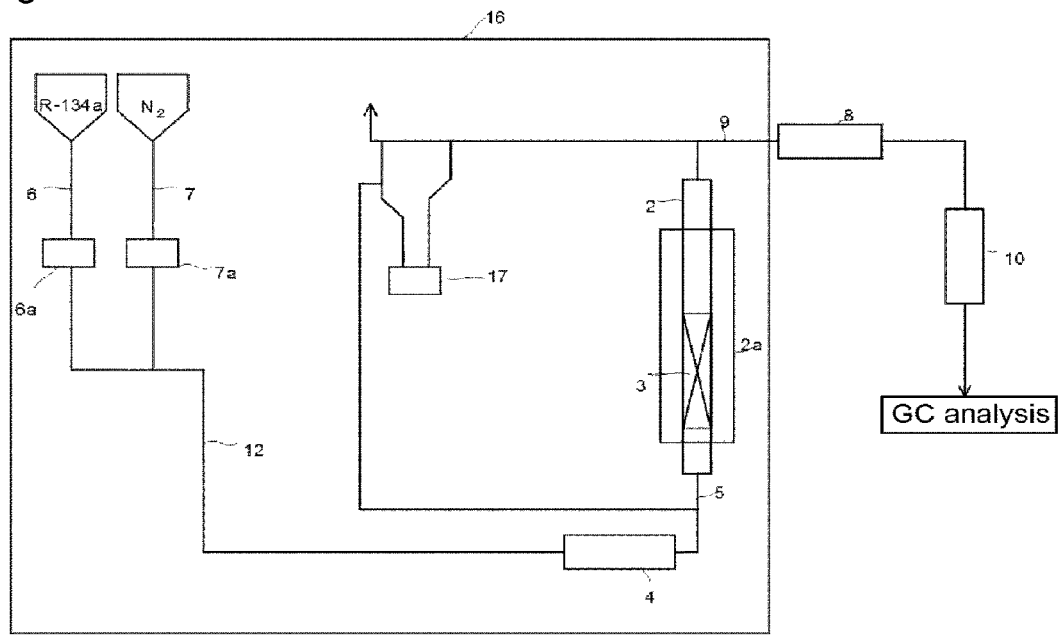
FIG. 16 is a diagram illustrating a fluidized bed reaction apparatus provided with a differential pressure measuring device used in Examples of the present invention.

As a reaction apparatus 2, a fluidized bed reaction apparatus 16 shown in FIG. 16 was used. The fluidized bed reaction apparatus 16 shown in FIG. 16 comprises the fluidized bed reaction apparatus 1 shown in FIG. 1, provided with a differential pressure measuring device to measure a differential pressure between on the inlet side and on the outlet side of the fluidized bed reactor 2.

In the fluidized bed reaction apparatus 16, as the fluidized bed reactor 2, a reactor for a vertical fluidized bed having an inner diameter of 106.3 mm and a height of 550 mm made of stainless steel (SUS316) was used, a SUS316 insertion tube having a diameter of 6 mm was introduced in the vertical direction of the reactor, a type K thermocouple was inserted to the insertion tube, and the temperature in the reactor was measured. Further, a grating was disposed at the lowest portion of the fluidized bed reactor 2, and a solid reactant was packed thereon to form a solid reactant layer 3. The interior of the fluidized bed reactor 2 was heated by an electric heater 2a.

A preheating mixer 4 was connected to the lower portion of the fluidized bed reactor 2 via a material gas supply line 5. The material gas supply line 5 and the preheating mixer 4 were respectively heated to 200 to 450° C. by a ribbon heater. The apparatus was so constituted that HFC-134a and nitrogen as a diluent gas were mixed while their flow rates were adjusted respectively by mass flow controllers 6a and 7a provided to a HFC-134a supply line 6 and a diluent gas supply line 7, and the gas mixture was supplied to the preheating mixer 4 through a gas mixture supply line 12. The outlet gas containing a reaction product was continuously withdrawn from the upper portion of the fluidized bed reactor 2, collected in a sampling bag made of polyvinylidene fluoride (PVdF) (hereinafter referred to as PVdF bag), and subjected to composition analysis by means of gas chromatography (GC).

Further, the differential pressure measuring device was constituted as follows. That is, a digital differential pressure gauge 17 was disposed between an outlet side piping connected to the lower portion of the fluidized bed reactor 2 and an outlet side piping connected to the upper portion.

(Linear Velocity)

The linear velocity of each of the nitrogen gas, HFC-134a and the gas mixture of nitrogen and HFC-134a was obtained by dividing the flow rate (volume flow rate) per unit time of each gas at the reaction temperature under the reaction pressure by the cross section area of the fluidized bed reactor 2.

Blank Differential Pressure Measurement Example 1

The differential pressure when a nitrogen gas was made to flow through the empty fluidized bed reactor 2 before packed with the reactant of the fluidized bed reaction apparatus 16 at a flow rate of 3.92 mol/min (linear velocity of 18 cm/s) at room temperature (25° C.) under normal pressure was measured. On that occasion, the differential pressure between on the inlet side and on the outlet side of the fluidized bed reactor measured by the differential pressure gauge was 10,900 Pa. Then, the nitrogen gas flow rate was gradually decreased, and the differential pressure between on the inlet side and on the outlet side of the fluidized bed reactor was measured by the differential pressure gauge at each flow rate.

Blank Differential Pressure Measurement Example 2

The differential pressure when HFC-134a was made to flow through the empty fluidized bed reactor 2 before packed with the reactant of the fluidized bed reaction apparatus 16 at a flow rate of 2.61 mol/min (linear velocity of 12 cm/s) at room temperature (25° C.) under normal pressure was measured. On that occasion, the differential pressure between on the inlet side and on the outlet side of the fluidized bed reactor measured by the differential pressure gauge was 11,500 Pa. Then, the HFC-134a flow rate was gradually decreased, and the differential pressure between on the inlet side and on the outlet side of the fluidized bed reactor was measured by the differential pressure gauge at each flow rate.

Blank Differential Pressure Measurement Example 3

The differential pressure when a nitrogen gas was made to flow through the empty fluidized bed reactor 2 before packed with the reactant of the fluidized bed reaction apparatus 16 at a flow rate of 2.47 mol/min (linear velocity of 18 cm/s) at 200° C. under normal pressure was measured. On that occasion, the differential pressure between on the inlet side and on the outlet side of the fluidized bed reactor measured by the differential pressure gauge was 11,700 Pa. Then, the nitrogen gas flow rate was gradually decreased, and the differential pressure between on the inlet side and on the outlet side of the fluidized bed reactor was measured by the differential pressure gauge at each flow rate.

Blank Differential Pressure Measurement Example 4

The differential pressure when a nitrogen gas was made to flow through the empty fluidized bed reactor 2 before packed with the reactant of the fluidized bed reaction apparatus 16 at a flow rate of 1.25 mol/min (linear velocity of 11 cm/s) at 300° C. under normal pressure was measured. On that occasion, the differential pressure between on the inlet side and on the outlet side of the fluidized bed reactor measured by the differential pressure gauge was 6,500 Pa. Then, the nitrogen gas flow rate was gradually decreased, and the differential pressure between on the inlet side and on the outlet side of the fluidized bed reactor was measured by the differential pressure gauge at each flow rate.

Reactant Packing Example 5

The fluidized bed reactor 2 of the fluidized bed reaction apparatus 16 was packed with 2,099 g (37.42 mol) of particulate calcium oxide (average particle size: 100 μm, bulk density: 1.2 g/cm$^3$, specific surface area: 2.9 m$^2$/g (hereinafter referred to as calcium oxide)) as a solid reactant to a height of 200 mm.

Reactant Packing Example 6

The fluidized bed reactor 2 of the fluidized bed reaction apparatus 16 was packed with 3,143 g (56.05 mol) of particulate calcium oxide (average particle size: 100 μm, bulk density: 1.2 g/cm$^3$, specific surface area: 2.9 m$^2$/g (hereinafter referred to as calcium oxide)) as a solid reactant to a height of 300 mm.

In the following Fluidization Examples 8 to 12, the fluidization starting velocity was determined in accordance with the calculated differential pressure obtained by subtracting the blank differential pressure before packing with the reactant from the differential pressure after packing with the reactant (hereinafter referred to as differential pressure after packing) under the same conditions (the temperature, the pressure, the type of the gas, the flow rate). In a graph obtained by plotting the calculated differential pressure relative to the linear velocity of the gas, the inflection point at which the gradient of the graph changes is taken as the starting point of fluidization of the solid reactant layer, and the linear velocity at the inflection point may be taken as the fluidization starting velocity. Further, in a graph having two inflection points in the differential pressure, the linear velocity at an inflection point on the lower linear velocity side is taken as the partial fluidization starting velocity, and the linear velocity at an inflection point on the higher linear velocity side is taken as the complete fluidization starting velocity.

Fluidization Example 8

Through the fluidized bed reaction apparatus packed with the solid reactant (calcium oxide having an average particle size of 100 μm) to a height of 200 mm shown in Reactant Packing Example 5, a nitrogen gas was made to flow at a flow rate of 3.05 mol/min (linear velocity of 14 cm/s) at room temperature (25° C.) under normal pressure. On that occasion, the differential pressure between on the inlet side and on the outlet side of the fluidized bed reactor measured by the differential pressure gauge was 10,900 Pa.

Figure 17:
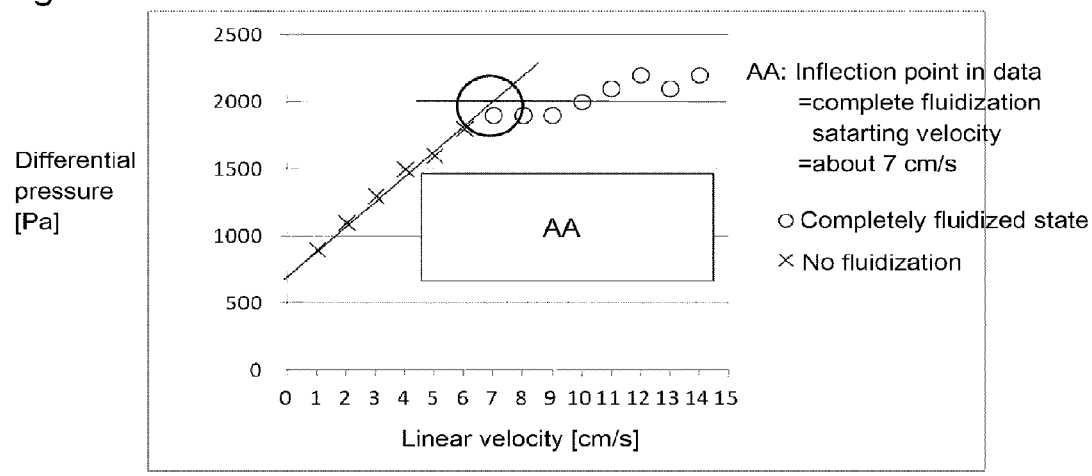
FIG. 17 is a graph obtained by plotting a differential pressure relative to a linear velocity of a nitrogen gas in Fluidization Example 8.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the differential pressure after packing, and the calculated differential pressure obtained by calculating the difference with the Blank Differential Pressure Measurement Example 1 are shown in Table 16. Further, a graph obtained by plotting the calculated differential pressure relative to the linear velocity of the nitrogen gas is shown in FIG. 17. It can be judged from Table 16 and FIG. 17 that in Fluidization Example 8, the complete fluidization starting velocity of the solid reactant layer is 7 cm/s.

TABLE 16

| | | Fluidization Example 8 | | | | | | |
|---|---|---|---|---|---|---|---|---|
| Type of reactant ° C. | | Calcium oxide | | | | | | |
| Reactant packing height mm | | 200 | | | | | | |
| Temperature ° C. | | 25 | | | | | | |
| Gas composition | HFC-134a mol % | 0 | | | | | | |
| ratio | Nitrogen mol % | 100 | | | | | | |
| Flow rate | HFC-134a mol/min | 0.00 | 0.00 | 0.00 | 0.00 | 0.00 | 0.00 | 0.00 |
| | Nitrogen mol/min | 3.05 | 2.83 | 2.61 | 2.39 | 2.18 | 1.96 | 1.74 |
| Linear velocity cm/s | | 14 | 13 | 12 | 11 | 10 | 9 | 8 |
| Differential pressure after packing Pa | | 10900 | 10000 | 9300 | 8500 | 7700 | 6900 | 6100 |
| Blank differential pressure Pa | | 8700 | 7900 | 7100 | 6400 | 5700 | 5000 | 4200 |
| Calculated differential pressure Pa | | 2200 | 2100 | 2200 | 2100 | 2000 | 1900 | 1900 |

| | | Fluidization Example 8 | | | | | | |
|---|---|---|---|---|---|---|---|---|
| Type of reactant ° C. | | Calcium oxide | | | | | | |
| Reactant packing height mm | | 200 | | | | | | |
| Temperature ° C. | | 25 | | | | | | |
| Gas composition | HFC-134a mol % | 0 | | | | | | |
| ratio | Nitrogen mol % | 100 | | | | | | |
| Flow rate | HFC-134a mol/min | 0.00 | 0.00 | 0.00 | 0.00 | 0.00 | 0.00 | 0.00 |
| | Nitrogen mol/min | 1.52 | 1.31 | 1.09 | 0.87 | 0.65 | 0.44 | 0.22 |
| Linear velocity cm/s | | 7 | 6 | 5 | 4 | 3 | 2 | 1 |
| Differential pressure after packing Pa | | 5400 | 4700 | 3900 | 3300 | 2500 | 1900 | 1200 |
| Blank differential pressure Pa | | 3500 | 2900 | 2300 | 1800 | 1200 | 800 | 300 |
| Calculated differentialpressure Pa | | 1900 | 1800 | 1600 | 1500 | 1300 | 1100 | 900 |

* Blank Differential Pressure Measurement Example 1 was employed.

Fluidization Example 9

Through the fluidized bed reaction apparatus packed with the solid reactant (calcium oxide having an average particle size of 100 μm) to a height of 300 mm shown in Reactant Packing Example 6, a nitrogen gas was made to flow at a flow rate of 2.83 mol/min (linear velocity of 13 cm/s) at room temperature (25° C.) under normal pressure. On that occasion, the differential pressure between on the inlet side and on the outlet side of the fluidized bed reactor measured by the differential pressure gauge was 10,200 Pa.

Figure 18:
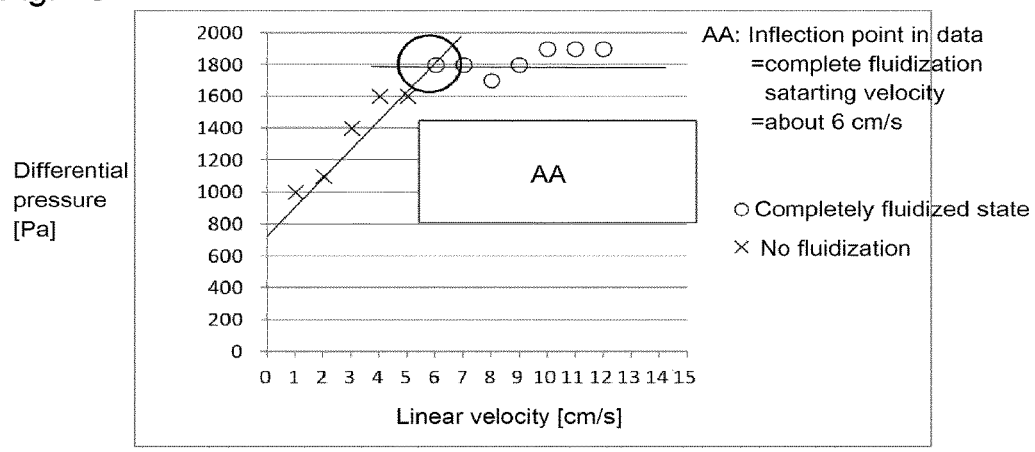
FIG. 18 is a graph obtained by plotting a differential pressure relative to a linear velocity of a nitrogen gas in Fluidization Example 9.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the differential pressure after packing, and the calculated differential pressure obtained by calculating the difference with the Blank Differential Pressure Measurement Example 1 are shown in Table 17. Further, a graph obtained by plotting the calculated differential pressure relative to the linear velocity of the nitrogen gas is shown in FIG. 18. It can be judged from Table 17 and FIG. 18 that in Fluidization Example 9, the complete fluidization starting velocity of the solid reactant layer is 5 cm/s.

TABLE 17

Fluidization Example 9

| | | | | | | | | |
|---|---|---|---|---|---|---|---|---|
| Type of reactant ° C. | | Calcium oxide | | | | | | |
| Reactant packing height mm | | 300 | | | | | | |
| Temperature ° C. | | 25 | | | | | | |
| Gas composition | HFC-134a mol % | 0 | | | | | | |
| ratio | Nitrogen mol % | 100 | | | | | | |
| Flow rate | HFC-134a mol/min | 0.00 | 0.00 | 0.00 | 0.00 | 0.00 | 0.00 | 0.00 |
| | Nitrogen mol/min | 2.83 | 2.61 | 2.39 | 2.18 | 1.96 | 1.74 | 1.52 |
| Linear velocity cm/s | | 13 | 12 | 11 | 10 | 9 | 8 | 7 |
| Differential pressure after packing Pa | | 10200 | 9400 | 8600 | 7800 | 7100 | 6400 | 5700 |
| Blank differential pressure Pa | | 7900 | 7100 | 6400 | 5700 | 5000 | 4200 | 3500 |
| Calculated differential pressure Pa | | 2300 | 2300 | 2200 | 2100 | 2100 | 2200 | 2200 |

Fluidization Example 9

| | | | | | | | |
|---|---|---|---|---|---|---|---|
| Type of reactant ° C. | | Calcium oxide | | | | | |
| Reactant packing height mm | | 300 | | | | | |
| Temperature ° C. | | 25 | | | | | |
| Gas composition | HFC-134a mol % | 0 | | | | | |
| ratio | Nitrogen mol % | 100 | | | | | |
| Flow rate | HFC-134a mol/min | 0.00 | 0.00 | 0.00 | 0.00 | 0.00 | 0.00 |
| | Nitrogen mol/min | 1.31 | 1.09 | 0.87 | 0.65 | 0.44 | 0.22 |
| Linear velocity cm/s | | 6 | 5 | 4 | 3 | 2 | 1 |
| Differential pressure after packing Pa | | 5000 | 4400 | 3700 | 3100 | 2500 | 1900 |
| Blank differential pressure Pa | | 2900 | 2300 | 1800 | 1200 | 800 | 300 |
| Calculated differential pressure Pa | | 2100 | 2100 | 1900 | 1900 | 1700 | 1600 |

* Blank Differential Pressure Measurement Example 1 was employed.

Fluidization Example 10

Through the fluidized bed reaction apparatus packed with the solid reactant (calcium oxide having an average particle size of 100 μm) to a height of 200 mm shown in Reactant Packing Example 5, HFC-134a was made to flow at a flow rate of 2.61 mol/min (linear velocity of 12 cm/s) at room temperature (25° C.) under normal pressure. On that occasion, the differential pressure between on the inlet side and on the outlet side of the fluidized bed reactor measured by the differential pressure gauge was 13,400 Pa.

Figure 19:
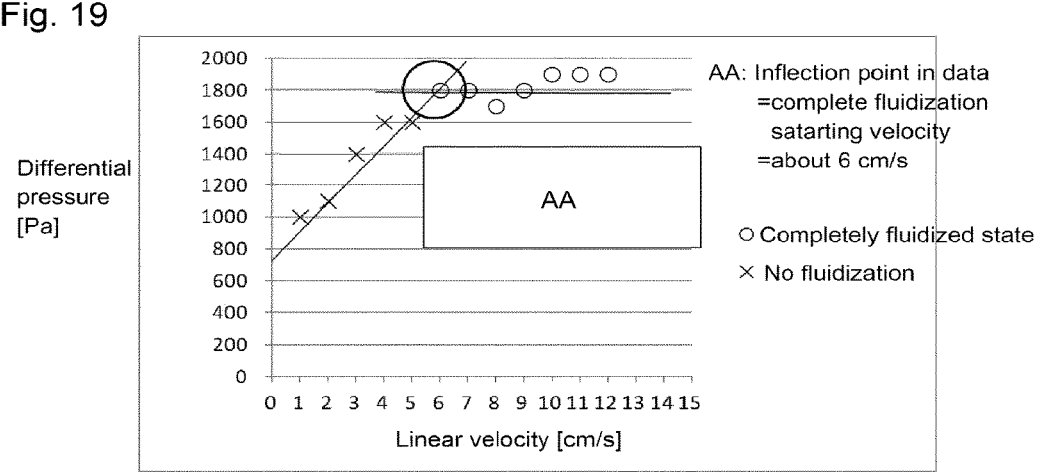
FIG. 19 is a graph obtained by plotting a differential pressure relative to a linear velocity of HFC-134a in Fluidization Example 10.

Then, the HFC-134a flow rate was gradually decreased, and the differential pressure between on the inlet side and on the outlet side of the fluidized bed reactor was measured by the differential pressure gauge at each flow rate. The flow rate of HFC-134a, the linear velocity, the differential pressure after packing, and the calculated differential pressure obtained by calculating the difference with the Blank Differential Pressure Measurement Example 2 are shown in Table 18. Further, a graph obtained by plotting the calculated differential pressure relative to the linear velocity of HFC-134a is shown in FIG. 19. It can be judged from Table 18 and FIG. 19 that in Fluidization Example 10, the complete fluidization starting velocity of the solid reactant layer is 6 cm/s.

TABLE 18

Fluidization Example 10

| | | | | | | | |
|---|---|---|---|---|---|---|---|
| Type of reactant ° C. | | Calcium oxide | | | | | |
| Reactant packing height mm | | 200 | | | | | |
| Temperature ° C. | | 25 | | | | | |
| Gas composition | HFC-134a mol % | 100 | | | | | |
| ratio | Nitrogen mol % | 0 | | | | | |
| Flow rate | HFC-134a mol/min | 2.61 | 2.39 | 2.18 | 1.96 | 1.74 | 1.52 |
| | Nitrogen mol/min | 0.00 | 0.00 | 0.00 | 0.00 | 0.00 | 0.00 |
| Linear velocity cm/s | | 12 | 11 | 10 | 9 | 8 | 7 |
| Differential pressure after packing Pa | | 13400 | 12200 | 10900 | 9600 | 8400 | 7200 |
| Blank differential pressure Pa | | 11500 | 10300 | 9000 | 7800 | 6700 | 5400 |
| Calculated differential pressure Pa | | 1900 | 1900 | 1900 | 1800 | 1700 | 1800 |

Fluidization Example 10

| | | | | | | | |
|---|---|---|---|---|---|---|---|
| Type of reactant ° C. | | Calcium oxide | | | | | |
| Reactant packing height mm | | 200 | | | | | |
| Temperature ° C. | | 25 | | | | | |
| Gas composition | HFC-134a mol % | 100 | | | | | |
| ratio | Nitrogen mol % | 0 | | | | | |
| Flow rate | HFC-134a mol/min | 1.31 | 1.09 | 0.87 | 0.65 | 0.44 | 0.22 |
| | Nitrogen mol/min | 0.00 | 0.00 | 0.00 | 0.00 | 0.00 | 0.00 |
| Linear velocity cm/s | | 6 | 5 | 4 | 3 | 2 | 1 |
| Differential pressure after packing Pa | | 6200 | 5000 | 3900 | 2900 | 2000 | 1300 |
| Blank differential pressure Pa | | 4400 | 3400 | 2300 | 1500 | 900 | 300 |
| Calculated differential pressure Pa | | 1800 | 1600 | 1600 | 1400 | 1100 | 1000 |

* Blank Differential Pressure Measurement Example 2 was employed.

Fluidization Example 11

Through the fluidized bed reaction apparatus packed with the solid reactant (calcium oxide having an average particle size of 100 μm) to a height of 200 mm shown in Reactant Packing Example 5, a nitrogen gas was made to flow at a flow rate of 2.19 mol/min (linear velocity of 16 cm/s) at 200° C. under normal pressure. On that occasion, the differential pressure between on the inlet side and on the outlet side of the fluidized bed reactor measured by the differential pressure gauge was 1,200 Pa.

Figure 20:
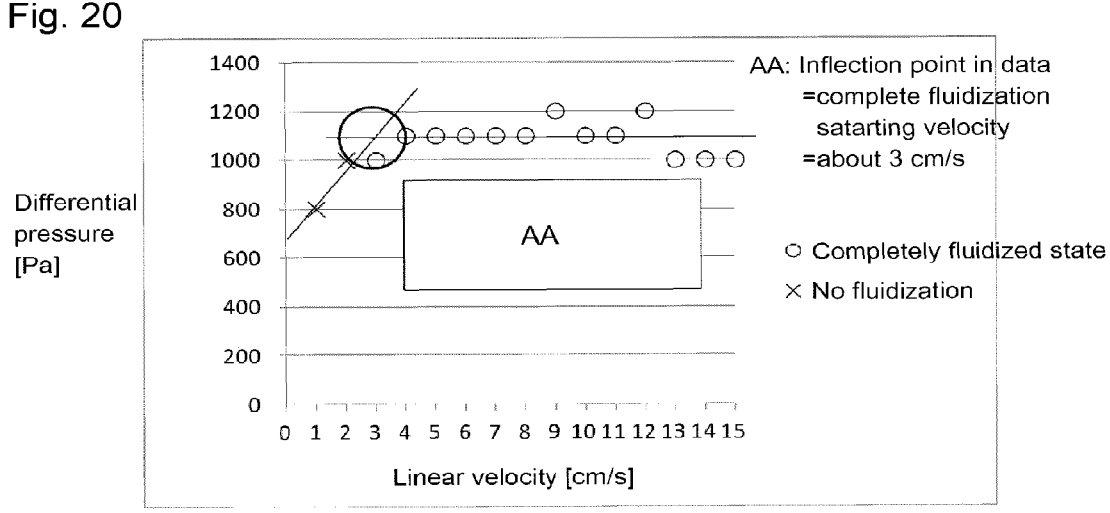
FIG. 20 is a graph obtained by plotting a differential pressure relative to a linear velocity of a nitrogen gas in Fluidization Example 11.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the differential pressure after packing, and the calculated differential pressure obtained by calculating the difference with the Blank Differential Pressure Measurement Example 3 are shown in Table 19. Further, a graph obtained by plotting the calculated differential pressure relative to the linear velocity of the nitrogen gas is shown in FIG. 20. It can be judged from Table 19 and FIG. 20 that in Fluidization Example 11, the complete fluidization starting velocity of the solid reactant layer is 3 cm/s.

TABLE 19

| | | Fluidization Example 11 | | | | | | | |
|---|---|---|---|---|---|---|---|---|---|
| Type of reactant ° C. | | Calcium oxide | | | | | | | |
| Reactant packing height mm | | 200 | | | | | | | |
| Temperature ° C. | | 200 | | | | | | | |
| Gas composition | HFC-134a mol % | 0 | | | | | | | |
| ratio | Nitrogen mol % | 100 | | | | | | | |
| Flow rate | HFC-134a mol/min | 0.00 | 0.00 | 0.00 | 0.00 | 0.00 | 0.00 | 0.00 | 0.00 |
| | Nitrogen mol/min | 2.19 | 2.06 | 1.92 | 1.78 | 1.65 | 1.51 | 1.37 | 1.23 |
| Linear velocity cm/s | | 16 | 15 | 14 | 13 | 12 | 11 | 10 | 9 |
| Differential pressure after packing Pa | | 11200 | 10500 | 9800 | 9100 | 8500 | 7700 | 7000 | 6300 |
| Blank differential pressure Pa | | 10100 | 9500 | 8800 | 8100 | 7300 | 6600 | 5900 | 5100 |
| Calculated differential pressure Pa | | 1100 | 1000 | 1000 | 1000 | 1200 | 1100 | 1100 | 1200 |

| | | Fluidization Example 11 | | | | | | | |
|---|---|---|---|---|---|---|---|---|---|
| Type of reactant ° C. | | Calcium oxide | | | | | | | |
| Reactant packing height mm | | 200 | | | | | | | |
| Temperature ° C. | | 200 | | | | | | | |
| Gas composition | HFC-134a mol % | 0 | | | | | | | |
| ratio | Nitrogen mol % | 100 | | | | | | | |
| Flow rate | HFC-134a mol/min | 0.00 | 0.00 | 0.00 | 0.00 | 0.00 | 0.00 | 0.00 | 0.00 |
| | Nitrogen mol/min | 1.10 | 0.96 | 0.82 | 0.69 | 0.55 | 0.41 | 0.27 | 0.14 |
| Linear velocity cm/s | | 8 | 7 | 6 | 5 | 4 | 3 | 2 | 1 |
| Differential pressure after packing Pa | | 5600 | 4900 | 4300 | 3700 | 3100 | 2400 | 1900 | 1200 |
| Blank differential pressure Pa | | 4500 | 3800 | 3200 | 2600 | 2000 | 1400 | 900 | 400 |
| Calculated differential pressure Pa | | 1100 | 1100 | 1100 | 1100 | 1100 | 1000 | 1000 | 800 |

\* Blank Differential Pressure Measurement Example 3 was employed.

Fluidization Example 12

Through the fluidized bed reaction apparatus packed with the solid reactant (calcium oxide having an average particle size of 100 μm) to a height of 200 mm shown in Reactant Packing Example 5, a nitrogen gas was made to flow at a flow rate of 1.25 mol/min (linear velocity of 11 cm/s) at 300° C. under normal pressure. On that occasion, the differential pressure between on the inlet side and on the outlet side of the fluidized bed reactor measured by the differential pressure gauge was 7,700 Pa.

Figure 21:
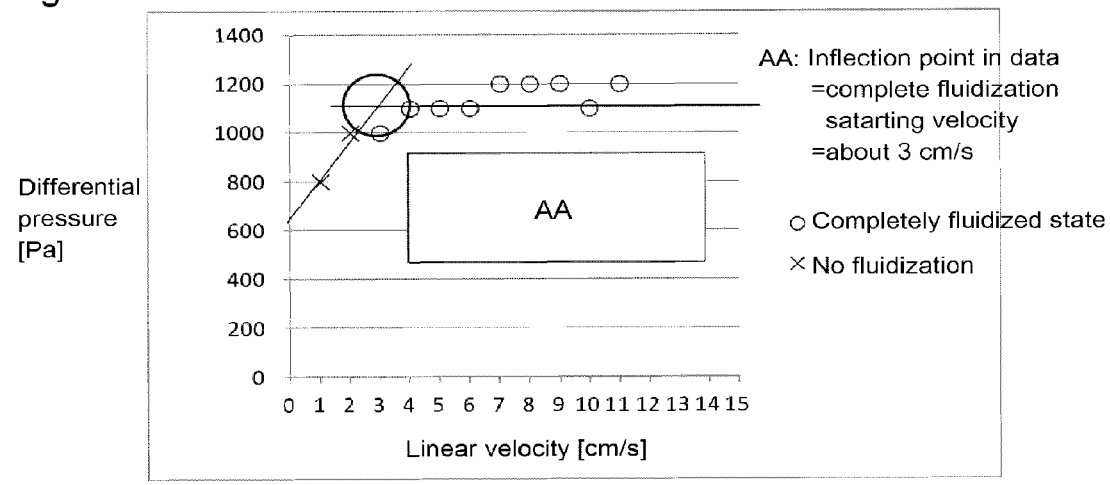
FIG. 21 is a graph obtained by plotting a differential pressure relative to a linear velocity of a nitrogen gas in Fluidization Example 12.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the differential pressure after packing, and the calculated differential pressure obtained by calculating the difference with the Blank Differential pressure Measurement Example 4 are shown in Table 20. Further, a graph obtained by plotting the calculated differential pressure relative to the linear velocity of the nitrogen gas is shown in FIG. 21. It can be judged from Table 20 and FIG. 21 that in Fluidization Example 12, the complete fluidization starting velocity of the solid reactant layer is 3 cm/s.

TABLE 20

| | Fluidization Example 12 | | | | | | | | | | |
|---|---|---|---|---|---|---|---|---|---|---|---|
| Type of reactant ° C. | Calcium oxide | | | | | | | | | | |
| Reactant packing height mm | 200 | | | | | | | | | | |
| Temperature ° C. | 300 | | | | | | | | | | |
| Gas composition HFC-134a mol % | 0 | | | | | | | | | | |
| ratio Nitrogen mol % | 100 | | | | | | | | | | |
| Flow rate HFC-134a mol/min | 0.00 | 0.00 | 0.00 | 0.00 | 0.00 | 0.00 | 0.00 | 0.00 | 0.00 | 0.00 | 0.00 |
| Nitrogen mol/min | 1.25 | 1.13 | 1.02 | 0.91 | 0.79 | 0.68 | 0.57 | 0.45 | 0.34 | 0.23 | 0.11 |
| Linear velocity cm/s | 11 | 10 | 9 | 8 | 7 | 6 | 5 | 4 | 3 | 2 | 1 |
| Differential pressure after packing Pa | 7700 | 7000 | 6300 | 5700 | 5000 | 4300 | 3700 | 3100 | 2500 | 1900 | 1200 |
| Blank differential pressure Pa | 6500 | 5900 | 5100 | 4500 | 3800 | 3200 | 2600 | 2000 | 1500 | 900 | 400 |
| Calculated differential pressure Pa | 1200 | 1100 | 1200 | 1200 | 1200 | 1100 | 1100 | 1100 | 1000 | 1000 | 800 |

* Blank Differential Pressure Measurement Example 4 was employed.

The results of the fluidization tests in the above Fluidization Examples 8 to 12 are shown in Table 21. It is found from Table 21 that calcium oxide having an average particle size of 100 μm has favorable flowability, and it can be in a fluidized state by making a gas to flow therethrough at a linear velocity of at least 7 cm/s regardless of the type of the gas and the packing height. Further, it is found that the flowability increases as the temperature increases.

TABLE 21

| | Fluidization Example 8 | Fluidization Example 9 | Fluidization Example 10 | Fluidization Example 11 | Fluidization Example 12 |
|---|---|---|---|---|---|
| Reactant Packing Example | Packing Example 5 | Packing Example 6 | Packing Example 5 | Packing Example 5 | Packing Example 5 |
| Average particle size of calcium oxide μm | 100 | 100 | 100 | 100 | 100 |
| Fluidization visualized test apparatus or fluidized bed reaction apparatus | Fluidized bed reaction apparatus | Fluidized bed reaction apparatus | Fluidized bed reaction apparatus | Fluidized bed reaction apparatus | Fluidized bed reaction apparatus |
| Temperature ° C. | 25 | 25 | 25 | 200 | 300 |
| Gas composition HFC-134a mol % | 0 | 0 | 100 | 0 | 0 |
| ratio Nitrogen mol % | 100 | 100 | 0 | 100 | 100 |
| Linear velocity/ Partial fluidization starting velocity | Nil | Nil | Nil | Nil | Nil |
| differential pressure plot analysis Complete fluidization starting velocity | 7 cm/s | 5 cm/s | 6 cm/s | 3 cm/s | 3 cm/s |

Examples 3 to 10

First, in Example 3, the interior of the fluidized bed reactor of the fluidized bed reaction apparatus packed with the solid reactant (calcium oxide having an average particle size of 100 μm) to a height of 300 mm shown in Reactant Packing Example 6 was heated to 300° C. by an electric furnace. Then, a nitrogen gas was made to flow through the fluidized bed reaction apparatus at a flow rate of 0.79 mol/min (linear velocity of 7 cm/s) under normal pressure. From the results of the above Fluidization Examples 8 to 12, it is considered that the layer of calcium oxide was in a completely fluidized state at this linear velocity.

Then, the flow rate of the nitrogen gas was decreased to 0.71 mol/min and at the same time, HFC-134a was started to be made to flow at a flow of 0.08 mmol/min. HFC-134a was made to flow and reacted for 2 minutes from the start of the flow of HFC-134a, and then the supply of HFC-134a was terminated and at the same time, the flow rate of the nitrogen gas was changed to 0.79 mol/min, and the reaction in Example 3 was completed. The outlet gas for about 10 seconds from 2 minutes after the start of the flow of HFC-134a to the completion of the reaction was continuously collected in a PVdF bag.

Then, after completion of the reaction in Example 3, without exchanging calcium oxide in the fluidized bed reactor, Examples 4 to 10 were carried out as it was. In Examples 4 to 10, HFC-134a was brought into contact with and reacted with the solid reactant in the same manner as in Example 3 except that the reaction conditions were as identified in Table 22. Further, the composition of the outlet gas collected in the PVdF bag was analyzed by gas chromatography (GC). The analysis results are shown in Table 22 together with the reaction conditions (the nitrogen flow rate before the reaction, the reaction temperature, the HFC-134a flow rate at the time of the reaction, the nitrogen flow rate at the time of the reaction, the composition at the time of the reaction (HFC-134a:nitrogen (molar ratio)), the linear velocity at the time of the reaction, the contact time at the time of the reaction, presence or absence of the fluidized state at the time of the reaction, and the reaction time).

Examples 11 to 15

First, in Example 1, the interior of the fluidized bed reactor of the fluidized bed reaction apparatus packed with the solid reactant (calcium oxide having an average particle size of 100 μm) to a height of 300 mm shown in Reactant Packing Example 6 was heated to 350° C. by an electric furnace. And, a nitrogen gas was made to flow through the fluidized bed reaction apparatus at a flow rate of 0.73 mmol/min (linear velocity of 7 cm/s) under normal pressure. From the results of the above Comparative Fluidization Examples 8 to 12, it is considered that the layer of calcium oxide was in a completely fluidized state at this linear velocity.

Then, simultaneously with termination of the flow of the nitrogen gas, HFC-134a was started to be made to flow at a flow rate of 0.73 5 mmol/min. HFC-134a was made to flow and reacted for 3 minutes from the start of the flow of HFC-134a, and only the supply of HFC-134a was terminated and at the same time, the flow rate of the nitrogen gas was changed to 0.73 mol/min, to complete the reaction in Example 11. The outlet gas was continuously collected in a PVdF bag for about 10 seconds from 5 minutes after the start of the flow of HFC-134a to the completion of the reaction.

Then, after completion of the reaction in Example 11, without exchanging potassium calcium oxide in the fluidized bed reactor, Examples 12 to 15 were conducted as it was. In Examples 12 to 15, HFC-134a was brought into contact with and reacted with the solid reactant in the same manner as in Example 11 except that the reaction conditions were as identified in Table 23. And, the composition of the outlet gas collected in the PVdF bag was analyzed by gas chromatography (GC). The analysis results are shown in Table 23 together with the reaction conditions (the nitrogen flow rate before the reaction, the reaction temperature, the HFC-134a flow rate at the time of the reaction, the nitrogen flow rate at the time of the reaction, the composition at the time of the reaction (HFC-134a:nitrogen (molar ratio)), the linear velocity at the time of the reaction, the contact time at the time of the reaction, presence or absence of the fluidized state at the time of the reaction, and the reaction time).

Then, in Examples 3 to 10 and 11 to 15, based on the molar ratio (mol %) calculated from the area ratio of the outlet gas obtained by gas chromatography analysis, the degree of conversion (reactivity) of HFC-134a, the selectivity for HFO-1123 and the selectivity for other gases were obtained as follows. In the following reaction formulae, (HFC-134a) and (HFO-1123) respectively represent the molar ratios (mol %) of (HFC-134a) and (HFO-1123) in the outlet gas.

The results are shown in the lower rows in Table 22 with respect to Examples 3 to 10 and in the lower rows in Table 23 with respect to Examples 11 to 15.

[Degree of Conversion (%) of HFC-134a]

It represents the proportion of components other than HFC-134a among components derived from HFC-134a in the outlet gas. It is calculated from {100−(HFC-134a)}/100×100(%) in the outlet gas.

[Selectivity (%) for HFO-1123]

It represents the proportion of HFC-134a converted to HFO-1123 based on the entire HFC-134a reacted, represented by %. It is calculated from (HFO-1123)/{100−(HFC-134a)}×100(%) in the outlet gas.

[Selectivity (%) For Other Gases]

It represents the proportion of HFC-134a converted to compounds other than HFO-1123 based on the entire HFC-134a reacted, represented by %. It is calculated from {100−(HFC-134a)−(HFO-1123)}/{100−(HFC-134a)}×100(%) in the outlet gas.

TABLE 22

|  |  | Example 3 | Example 4 | Example 5 | Example 6 | Example 7 | Example 8 | Example 9 | Example 10 |
|---|---|---|---|---|---|---|---|---|---|
| Solid reactant | | Calcium oxide | | | | | | | |
| Reactant packing amount (g) | | 3143 | | | | | | | |
| Reactant packing amount (mol) | | 56.05 | | | | | | | |
| Nitrogen flow rate before reaction (mol/min) | | 0.79 | 0.76 | 0.73 | 0.70 | 0.67 | 0.65 | 0.63 | 0.61 |
| Reaction temperature (° C.) | | 300 | 325 | 350 | 375 | 400 | 425 | 450 | 475 |
| HFC-134a flow rate at the time of reaction (mol/min) | | 0.08 | 0.08 | 0.07 | 0.07 | 0.07 | 0.06 | 0.06 | 0.06 |
| Nitrogen flow rate at the time of reaction (mol/min) | | 0.71 | 0.76 | 0.66 | 0.63 | 0.61 | 0.59 | 0.57 | 0.55 |
| Composition ratio at the time of reaction HFC-134a:N2 (molar ratio) | | 10:90 | 10:90 | 10:90 | 10:90 | 10:90 | 10:90 | 10:90 | 10:90 |
| Linear velocity at the time of reaction (cm/s) | | 7 | 7 | 7 | 7 | 7 | 7 | 7 | 7 |
| Compact time at the time of reaction (s) | | 4.3 | 4.3 | 4.3 | 4.3 | 4.3 | 4.3 | 4.3 | 4.3 |
| Fluidized state at the time of reaction | | Completely fluidized state | | | | | | | |
| Reaction time (min) | | 2 | 2 | 2 | 2 | 2 | 2 | 2 | 2 |
| Structure | Name | Outlet gas composition (other than nitrogen) (mol %) | | | | | | | |
| CF2=CHF | HFO-1123 | 7.64 | 14.23 | 21.22 | 30.91 | 44.09 | 55.59 | 63.57 | 60.70 |
| CF3CH2F | HFC-134a | 92.30 | 85.71 | 78.68 | 68.80 | 55.07 | 41.88 | 29.35 | 22.86 |
| Others | | 0.1 | 0.1 | 0.1 | 0.3 | 0.8 | 2.5 | 7.1 | 16.4 |
| Degree of conversion of HFC-134a (%) | | 7.7 | 14.3 | 21.3 | 31.2 | 44.9 | 58.1 | 70.6 | 77.1 |
| Selectivity for HFO-1123 (%) | | 99.2 | 99.6 | 99.5 | 99.1 | 98.1 | 95.6 | 90.0 | 78.7 |
| Selectivity for other gases (%) | | 0.8 | 0.4 | 0.5 | 0.9 | 1.9 | 4.4 | 10.0 | 21.3 |

TABLE 23

|  | Example 11 | Example 12 | Example 13 | Example 14 | Example 15 |
|---|---|---|---|---|---|
| Solid reactant | Calcium oxide | | | | |
| Reactant packing amount (g) | 3143 | | | | |
| Reactant packing amount (mol) | 56.05 | | | | |
| Nitrogen flow rate before reaction (mol/min) | 0.73 | 0.70 | 0.67 | 0.65 | 0.63 |
| Reaction temperature (° C.) | 350 | 375 | 400 | 425 | 450 |
| HFC-134a flow rate at the time of reaction (mol/min) | 0.73 | 0.70 | 0.67 | 0.65 | 0.63 |
| Nitrogen flow rate at the time of reaction (mol/min) | 0.00 | 0.00 | 0.00 | 0.00 | 0.00 |
| Composition ratio at the time of reaction HFC-134a:N2 (molar ratio) | 100:0 | 100:0 | 100:0 | 100:0 | 100:0 |
| Linear velocity at the time of reaction (cm/s) | 7 | 7 | 7 | 7 | 7 |

TABLE 23-continued

|  | | Example 11 | Example 12 | Example 13 | Example 14 | Example 15 |
|---|---|---|---|---|---|---|
| Compact time at the time of reaction (s) | | 4.3 | 4.3 | 4.3 | 4.3 | 4.3 |
| Fluidized state at the time of reaction | | Completely fluidized state | | | | |
| Reaction time (min) | | 3 | 3 | 3 | 3 | 3 |
| Structure | Name | Outlet gas composition (other than nitrogen) (mol %) | | | | |
| $CF_2=CHF$ | HFO-1123 | 4.65 | 6.60 | 10.80 | 17.24 | 29.81 |
| $CF_3CH_2F$ | HFC-134a | 95.33 | 93.36 | 89.11 | 82.38 | 68.03 |
| Others | | 0.0 | 0.0 | 0.1 | 0.4 | 2.2 |
| Degree of conversion of HFC-134a (%) | | 4.7 | 6.6 | 10.9 | 17.6 | 32.0 |
| Selectivity for HFO-1123 (%) | | 99.5 | 99.5 | 99.2 | 97.9 | 93.3 |
| Selectivity for other gases (%) | | 0.5 | 0.5 | 0.8 | 2.1 | 6.7 |

As evident from Tables 14 and 15, the selectivity for HFO-1123 can be improved in Examples 1 and 2 in which HFC-134a was reacted with potassium carbonate in a fluidized state, as compared with Comparative Examples 1 and 2 in which HFC-134a was reacted with potassium carbonate not in a fluidized state. Further, as evident from Tables 21 and 22, HFO-1123 can be obtained with a high reactivity with a sufficiently high selectivity by reacting HFC-134a with calcium oxide in a fluidized state.

INDUSTRIAL APPLICABILITY

According to the production method of the present invention, HFO-1123 can be efficiently and stably produced from HFC-134a. The production method is useful as an industrial production method since HFC-134a which is an inexpensive material is used.

This application is a continuation of PCT Application No. PCT/JP2015/052527, filed on Jan. 29, 2015, which is based upon and claims the benefit of priority from Japanese Patent Application No. 2014-015962 filed on Jan. 30, 2014. The contents of those applications are incorporated herein by reference in their entireties.

REFERENCE SYMBOLS

1, 11, 16: Fluidized bed reaction apparatus, 2: fluidized bed reactor, 3: solid reactant layer, 4: preheating mixer, 5: material gas supply line, 6: HFC-134a supply line, 7: diluent gas supply line, 8: heating means, 9: outlet line, 10: hydrogen fluoride trapping tube, 12: gas mixture supply line, 13: differential pressure gauge, 14: visualized tester, 15: fluidization visualized test apparatus, 17: digital differential pressure gauge.

What is claimed is:

1. A method for producing trifluoroethylene, the method comprising:
passing a material gas containing 1,1,1,2-tetrafluoroethane through a layer consisting of a particulate solid reactant having an average particle size of from 1 μm to 5,000 μm to bring the solid reactant and 1,1,1,2-tetrafluoroethane into contact with each other in a state where the layer consisting of the solid reactant is fluidized,
wherein
the solid reactant contains at least one metal compound selected from the group consisting of a metal oxide, a metal hydroxide, a metal carbonate, a metal sulfate, and a metal halide,
the metal species contained in the metal compound is at least one metal selected from the group consisting of an alkali metal, an alkaline earth metal, a group 13 metal, and a group 14 metal, and
a linear flow velocity of the material gas is from 1 cm/s to 1,000 cm/s.

2. The method according to claim 1, wherein the solid reactant has an average particle size of from 40 μm to 500 μm.

3. The method according to claim 1, wherein the linear flow velocity of the material gas is from 1 cm/s to 20 cm/s.

4. The method according to claim 1, wherein the solid reactant is potassium carbonate and/or calcium oxide.

5. The method according to claim 1, wherein 1,1,1,2-tetrafluoroethane and the solid reactant are brought into contact with each other at a temperature of from 100° C. to 500° C.

6. The method according to claim 5, wherein 1,1,1,2-tetrafluoroethane and the solid reactant are brought into contact with each other at a temperature of from 350° C. to 500° C.

7. The method according to claim 1, wherein 1,1,1,2-tetrafluoroethane and the solid reactant are brought into contact with each other at a gauge pressure of from 0 to 5 MPa.

8. The method according to claim 1, wherein 1,1,1,2-tetrafluoroethane contacts the solid reactant for a period of time of from 0.1 second to 100 seconds.

9. The method according to claim 8, wherein the period of time is from 0.1 second to 20 seconds.

10. The method according to claim 1, wherein a content of 1,1,1,2-tetrafluoroethane in the material gas is from 1 mol % to 100 mol %.

11. The method according to claim 1, wherein the material gas further contains a diluent gas, and a content of the diluent gas is at most 95 mol % based on an entire amount of the material gas.

12. The method according to claim 1, wherein the material gas further contains 1,1,2,2-tetrafluoroethane, and a content of 1,1,2,2-tetrafluoroethane is less than 50 mol % based on a total amount of 1,1,1,2-tetrafluoroethane and 1,1,2,2-tetrafluoroethane.

* * * * *